(12) United States Patent
Al-Jilaihawi

(10) Patent No.: US 12,427,017 B2
(45) Date of Patent: Sep. 30, 2025

(54) METHODS, DEVICES AND SYSTEMS FOR TRANSCATHETER MITRAL VALVE REPLACEMENT IN A DOUBLE-ORIFICE MITRAL VALVE

(71) Applicant: CEDARS-SINAI MEDICAL CENTER, Los Angeles, CA (US)

(72) Inventor: Hasanian Al-Jilaihawi, Los Angeles, CA (US)

(73) Assignee: Cedars Sinai Medical Center, Los Angeles, CA (US)

( * ) Notice: Subject to any disclaimer, the term of this patent is extended or adjusted under 35 U.S.C. 154(b) by 427 days.

(21) Appl. No.: 17/081,146

(22) Filed: Oct. 27, 2020

(65) Prior Publication Data

US 2021/0038382 A1 Feb. 11, 2021

Related U.S. Application Data

(63) Continuation of application No. 15/101,362, filed as application No. PCT/US2014/069849 on Dec. 11, 2014, now Pat. No. 10,820,989.

(60) Provisional application No. 61/914,591, filed on Dec. 11, 2013.

(51) Int. Cl.
*A61F 2/24* (2006.01)

(52) U.S. Cl.
CPC .......... *A61F 2/2418* (2013.01); *A61F 2/2433* (2013.01); *A61F 2/2436* (2013.01); *A61F 2210/009* (2013.01); *A61F 2220/0025* (2013.01); *A61F 2220/0041* (2013.01); *A61F 2220/0091* (2013.01); *A61F 2230/001* (2013.01); *A61F 2250/006* (2013.01)

(58) Field of Classification Search
CPC .... A61F 2/2418; A61F 2/2433; A61F 2/2436; A61F 2210/009; A61F 2220/0025; A61F 2220/0041; A61F 2220/0091; A61F 2230/001; A61F 2250/006
See application file for complete search history.

(56) References Cited

U.S. PATENT DOCUMENTS

| 4,694,838 A | 9/1987 | Wijayarthna et al. |
| 4,738,667 A | 4/1988 | Galloway |
| 5,423,829 A | 6/1995 | Pham et al. |

(Continued)

FOREIGN PATENT DOCUMENTS

| CN | 1106647 A | 8/1995 |
| CN | 1647777 A | 8/2005 |

(Continued)

OTHER PUBLICATIONS

International Search Report and Written Opinion dated Feb. 10, 2015; 7 pages.

(Continued)

*Primary Examiner* — Brooke LaBranche
(74) *Attorney, Agent, or Firm* — Nixon Peabody LLP

(57) ABSTRACT

In various embodiments, provided herein are methods, devices and systems for transcatheter mitral valve replacement in a double-orifice mitral valve. These methods, devices and systems are used to treat patients with mitral valve disease, particularly those who have had failed edge-to-edge leaflet repair, or patients presently considered anatomically unsuitable for edge-to-edge leaflet repair alone.

20 Claims, 19 Drawing Sheets

(56) References Cited

U.S. PATENT DOCUMENTS

| | | |
|---|---|---|
| 5,833,632 A | 11/1998 | Jacobsen et al. |
| 5,964,744 A | 10/1999 | Balbierz et al. |
| 5,964,797 A | 10/1999 | Ho |
| 5,972,019 A | 10/1999 | Engelson et al. |
| 6,059,779 A | 5/2000 | Mills |
| 6,086,557 A | 7/2000 | Morejohn et al. |
| 6,168,614 B1 | 1/2001 | Andersen et al. |
| 6,217,611 B1 | 4/2001 | Klostermeyer |
| 6,287,277 B1 | 9/2001 | Yan |
| 6,350,282 B1 | 2/2002 | Eberhardt |
| 6,475,232 B1 | 11/2002 | Babbs |
| 6,589,230 B2 | 7/2003 | Gia et al. |
| 6,949,119 B2 | 9/2005 | Myers |
| 6,953,473 B2 | 10/2005 | Porter |
| 6,964,657 B2 | 11/2005 | Cragg et al. |
| 6,976,965 B2 | 12/2005 | Corl et al. |
| 7,134,994 B2 | 11/2006 | Alpert et al. |
| 7,150,758 B2 | 12/2006 | Kari |
| 7,340,288 B1 | 3/2008 | Karicherla et al. |
| 7,534,259 B2 | 5/2009 | Lashinski et al. |
| 7,935,144 B2 | 5/2011 | Robin et al. |
| 8,070,800 B2 | 12/2011 | Lock et al. |
| 8,092,524 B2 | 1/2012 | Nugent et al. |
| 8,372,069 B2 | 2/2013 | Kassab |
| 8,377,112 B2 | 2/2013 | Griffin et al. |
| 8,408,214 B2 | 4/2013 | Spenser |
| 8,430,927 B2 | 4/2013 | Bonhoeffer |
| 8,491,648 B2 | 7/2013 | Hassan et al. |
| 8,568,477 B2 | 10/2013 | Lashinksi et al. |
| 8,801,768 B2 | 8/2014 | Karwa |
| 9,427,216 B2 | 8/2016 | Szabo et al. |
| 2002/0169474 A1 | 11/2002 | Kusleika et al. |
| 2004/0073141 A1 | 4/2004 | Hartley et al. |
| 2004/0172081 A1 | 9/2004 | Wang |
| 2005/0203425 A1 | 9/2005 | Langston |
| 2005/0240200 A1 | 10/2005 | Bergheim |
| 2005/0256566 A1 | 11/2005 | Gabbay |
| 2005/0267010 A1 | 12/2005 | Goodson et al. |
| 2006/0064114 A1 | 3/2006 | Obitsu et al. |
| 2006/0155305 A1 | 7/2006 | Freudenthal |
| 2006/0287719 A1 | 12/2006 | Rowe et al. |
| 2007/0050021 A1 | 3/2007 | Johnson |
| 2007/0203562 A1 | 8/2007 | Malewicz et al. |
| 2008/0027334 A1 | 1/2008 | Langston |
| 2008/0033467 A1 | 2/2008 | Miyamoto et al. |
| 2008/0033541 A1* | 2/2008 | Gelbart .............. A61F 2/246 623/2.11 |
| 2008/0183273 A1 | 7/2008 | Mesana et al. |
| 2008/0221551 A1 | 9/2008 | Goodson et al. |
| 2008/0306499 A1 | 12/2008 | Katoh et al. |
| 2008/0319541 A1 | 12/2008 | Filsoufi |
| 2009/0082678 A1 | 3/2009 | Smith |
| 2009/0248143 A1 | 10/2009 | Laham |
| 2009/0259292 A1 | 10/2009 | Bonhoeffer |
| 2009/0276040 A1 | 11/2009 | Rowe et al. |
| 2010/0030330 A1 | 2/2010 | Bobo et al. |
| 2010/0076549 A1 | 3/2010 | Keidar et al. |
| 2010/0094209 A1 | 4/2010 | Drasler et al. |
| 2010/0168840 A1 | 7/2010 | Kassab |
| 2010/0185275 A1 | 7/2010 | Richter et al. |
| 2010/0191272 A1 | 7/2010 | Keating |
| 2010/0211094 A1 | 8/2010 | Sargent |
| 2010/0331948 A1 | 12/2010 | Turovskiy et al. |
| 2011/0098802 A1 | 4/2011 | Braido et al. |
| 2011/0137397 A1 | 6/2011 | Chau et al. |
| 2012/0059458 A1 | 3/2012 | Buchbinder et al. |
| 2012/0130230 A1 | 5/2012 | Eichler et al. |
| 2012/0158129 A1 | 6/2012 | Duffy et al. |
| 2012/0283757 A1 | 11/2012 | Miller et al. |
| 2012/0283812 A1 | 11/2012 | Lagodzki et al. |
| 2012/0283820 A1 | 11/2012 | Tseng et al. |
| 2012/0310328 A1 | 12/2012 | Olson et al. |
| 2012/0310330 A1 | 12/2012 | Buchbinder et al. |
| 2013/0090726 A1 | 4/2013 | Rowe et al. |
| 2013/0109960 A1 | 5/2013 | Stinis |
| 2013/0116779 A1 | 5/2013 | Weber |
| 2013/0166017 A1 | 6/2013 | Cartledge et al. |
| 2013/0190857 A1 | 7/2013 | Mitra et al. |
| 2013/0190865 A1 | 7/2013 | Anderson |
| 2013/0211509 A1 | 8/2013 | Spenser |
| 2013/0261738 A1 | 10/2013 | Clague et al. |
| 2013/0261739 A1* | 10/2013 | Kuehn .............. A61F 2/2412 623/2.11 |
| 2013/0274618 A1 | 10/2013 | Hou et al. |
| 2013/0331864 A1 | 12/2013 | Jelich et al. |
| 2013/0331921 A1 | 12/2013 | Roubin |
| 2014/0114402 A1 | 4/2014 | Ahlberg et al. |
| 2014/0135799 A1 | 5/2014 | Henderson |
| 2014/0171958 A1 | 6/2014 | Baig |
| 2014/0194981 A1 | 7/2014 | Menk et al. |
| 2014/0200662 A1 | 7/2014 | Eftel et al. |
| 2014/0222144 A1 | 8/2014 | Eberhardt et al. |
| 2014/0236287 A1 | 8/2014 | Clague et al. |
| 2014/0243966 A1 | 8/2014 | Garde et al. |
| 2014/0277419 A1 | 9/2014 | Garde et al. |
| 2014/0303719 A1 | 10/2014 | Cox et al. |
| 2014/0350669 A1 | 11/2014 | Gillespie et al. |
| 2016/0206424 A1 | 7/2016 | Al-Jilaihawi |
| 2016/0228013 A1 | 8/2016 | Al-Jilaihawi et al. |
| 2016/0228241 A1 | 8/2016 | Al-Jilaihawi |
| 2016/0235422 A1 | 8/2016 | Al-Jilaihawi et al. |
| 2016/0302920 A1 | 10/2016 | Al-Jilaihawi |
| 2016/0310699 A1 | 10/2016 | Al-Jilaihawi |
| 2018/0078363 A1 | 3/2018 | Al-Jilaihawi |
| 2021/0093448 A1 | 4/2021 | Al-Jilaihawi |

FOREIGN PATENT DOCUMENTS

| | | |
|---|---|---|
| CN | 101474102 A | 7/2009 |
| CN | 101489504 A | 7/2009 |
| CN | 101947146 A | 1/2011 |
| CN | 101972177 A | 2/2011 |
| CN | 103237523 A | 8/2013 |
| CN | 104220028 A | 12/2014 |
| CN | 104334119 A | 2/2015 |
| CN | 105611871 A | 5/2016 |
| CN | 105611889 A | 5/2016 |
| CN | 105744969 A | 7/2016 |
| CN | 105764447 A | 7/2016 |
| CN | 107405191 A | 11/2017 |
| EP | 2732796 A1 | 5/2014 |
| EP | 3054838 A1 | 8/2016 |
| EP | 3057522 A1 | 8/2016 |
| EP | 3079633 A1 | 10/2016 |
| EP | 3099345 A1 | 12/2016 |
| EP | 3267940 A1 | 1/2018 |
| WO | 1996017644 A1 | 6/1996 |
| WO | WO1998048879 | 11/1998 |
| WO | WO1999/15223 A1 | 4/1999 |
| WO | WO1999/15227 A1 | 4/1999 |
| WO | WO20020249511 | 6/2002 |
| WO | WO2005059379 A1 | 6/2005 |
| WO | WO2007081820 A1 | 7/2007 |
| WO | WO2010085659 A1 | 7/2010 |
| WO | WO2011039091 A1 | 4/2011 |
| WO | WO2012009675 A2 | 1/2012 |
| WO | WO2012161769 A1 | 11/2012 |
| WO | WO2012/173697 A1 | 12/2012 |
| WO | WO2013061281 A1 | 5/2013 |
| WO | WO2014145469 A1 | 9/2014 |
| WO | WO2015/054296 A1 | 4/2015 |
| WO | WO2015/057735 A1 | 4/2015 |
| WO | WO2015/057995 A2 | 4/2015 |
| WO | WO2015/058001 A1 | 4/2015 |
| WO | WO2015/089334 A1 | 6/2015 |
| WO | WO2015/117025 A1 | 8/2015 |
| WO | WO2016145250 A1 | 9/2016 |

OTHER PUBLICATIONS

International Search Report and Written Opinion dated Apr. 1, 2015; 10 pages.

(56) References Cited

OTHER PUBLICATIONS

International Search Report and Written Opinion dated Jan. 29, 2015; 6 pages.
International Search Report and Written Opinion dated Mar. 3, 2015; 9 pages.
International Search Report and Written Opinion dated Mar. 2, 2015; 8 pages.
International Search Report and Written Opinion dated Jun. 26, 2015; 10 pages.
Astarci et al. Transapical explantation of an embolized transcatheter valve. Interact Cardiovasc Thorac Surg (2011). 13:1-2.
Blows et al. The pressure wire in practice. Heart (2007). 93:419-422.
Bonhoeffer et al. The multi-track angiography catheter: a new tool for complex catheterisation in congenital heart disease. Heart (1996). 76:173-177.
Chiam et al. Percutaneous Transcatheter Mitral Valve Repair. J Am Coll Cardiol (2011). 4(1):1-13.
Ho, S.Y. Structure and anatomy of the aortic root. Eur J Echocardiogr (2009). 10:i3-i10.
Jolicoeur et al. Tiara: A Novel Catheter-Based Mitral Valve Bioprosthesis Initial Experiments and Short-Term Pre-Clinical Results. J Am Coll Cardiol (2012). 60(15):1430-1431.
Lange et al. Diagnostic Cardiac Catheterization. Circulation (2003). 107:e111-e113.
Masson et al. Percutaneous Treatment of Mitral Regurgitation. Circ Cardiovasc Interv (2009). 2:140-146.
McCarthy et al. Anatomy of the mitral valve: understanding the mitral valve complex in mitral regurgitation. Eur J Echocardiogr (2010). 11:i3-i9.
Ormiston et al. Bioabsorbable Coronary Stents (2009). Circ Cardiovasc Interv (2009). 2:255-260.
Sievers et al. The everyday used nomenclature of the aortic root components: the tower of Babel? Eur J Cardio-Thorac Surg (2011). 0:1-5.
Sinning et al. Aortic Regurgitation Index Defines Severity of Peri-Prosthetic Regurgitation and Predicts Outcome in Patients After Transcatheter Aortic Valve Implantation. J Am Coll Cardiol (2012). 59(13):1134-1141.
Tonino et al. Fractional Flow Reserve versus Angiography for Guiding Percutaneous Coronary Intervention. New Engl J Med (2009). 360(3):213-224.
Tsai et al. Transcatheter Retrieval of Dislodged Port-A Catheter Fragments: Experience with 47 Cases. Acta Cardiol Sin (2006). 22:221-228.
Van Mieghem et al. Anatomy of the Mitral Valvular Complex and Its Implications for Transcatheter Interventions for Mitral Regurgitation. J Am Coll Cardiol (2010). 56(8):617-626.
PCT/US2014/060526 International Preliminary Report on Patentability dated Apr. 19, 2016, 7 pages.
PCT/US2014/060957 International Preliminary Report on Patentability dated Apr. 19, 2016, 10 pages.
PCT/US2014/060966 International Preliminary Report on Patentability dated Apr. 19, 2016, 6 pages.
Extended European Search Report for EP Application No. 14853895.2 dated May 10, 2017, 8 pages.
Partial Supplementary European Search Report for EP Application No. 14851950.7 dated Apr. 10, 2017, 6 pages.
Extended European Search Report for EP Application No. 14869869.9 dated May 4, 2017, 7 pages.
PCT/US2016/021866 International Search Report and Written Opinion dated May 23, 2016, 11 pages.
PCT/US2016/021866 International Preliminary Report on Patentability dated Sep. 21, 2017, 9 pages.
EP16762555.7 Supplementary European Search Report dated Oct. 5, 2018, 8 pages.
Crushing. (n.d.) American Heritage Dictionary of the English Language, Fifth Edition, 2011, retrieved from https://thefreedictionary.com/crushing.
Compress. (n.d.) Merriam-Webster, 2018, retrieved from https://www.merriam-webster.com/dictionary/compressr.
EP 14869869.9 Examination Report dated Jan. 23, 2019, 4 pages.
PCT/US2014/069849 International Preliminary Report on Patentability dated Jun. 14, 2016, 7 pages.
PCT/US2014/059547 International Preliminary Report on Patentability dated Apr. 12, 2016, 7 pages.
EP 14851950.7 Examination Report dated May 24, 2018, 4 pages.
EP 14851950.7 Extended European Search Report dated Jul. 12, 2017, 10 pages.
EP 15743048.9 Extended Search Report dated Aug. 24, 2017, 8 pages.

* cited by examiner

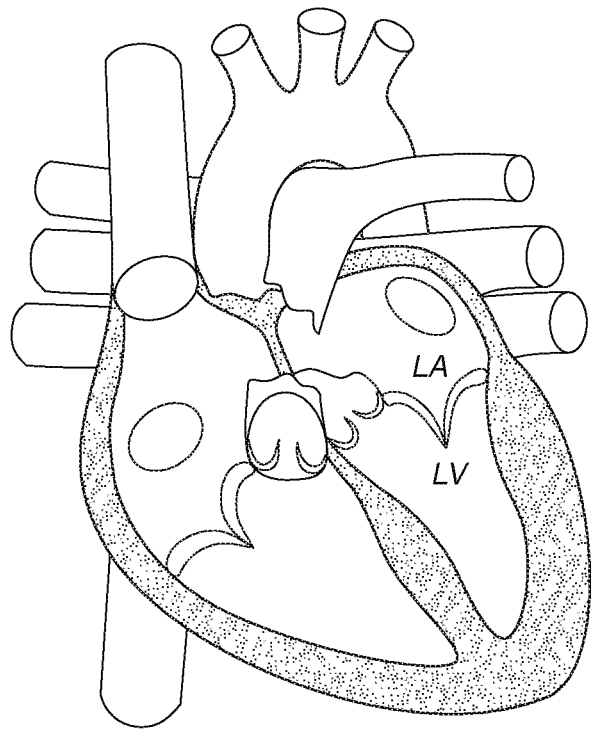
Fig. 1A1
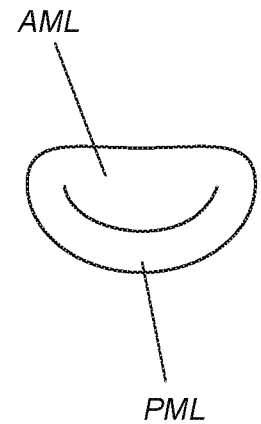
Fig. 1A2
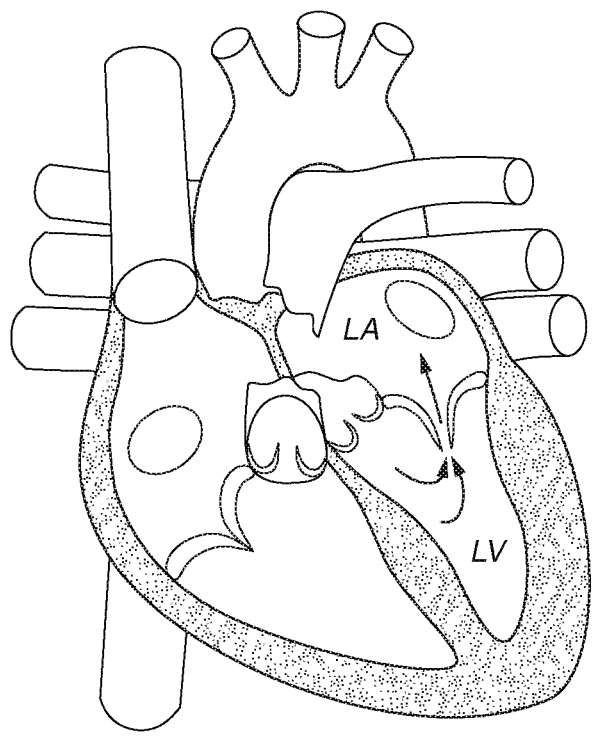
Fig. 1B1
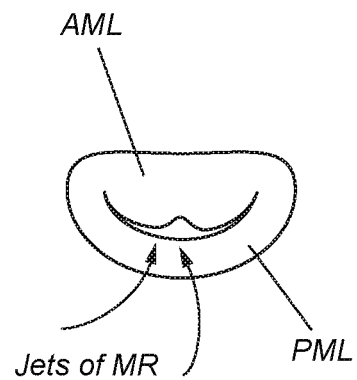
Fig. 1B2

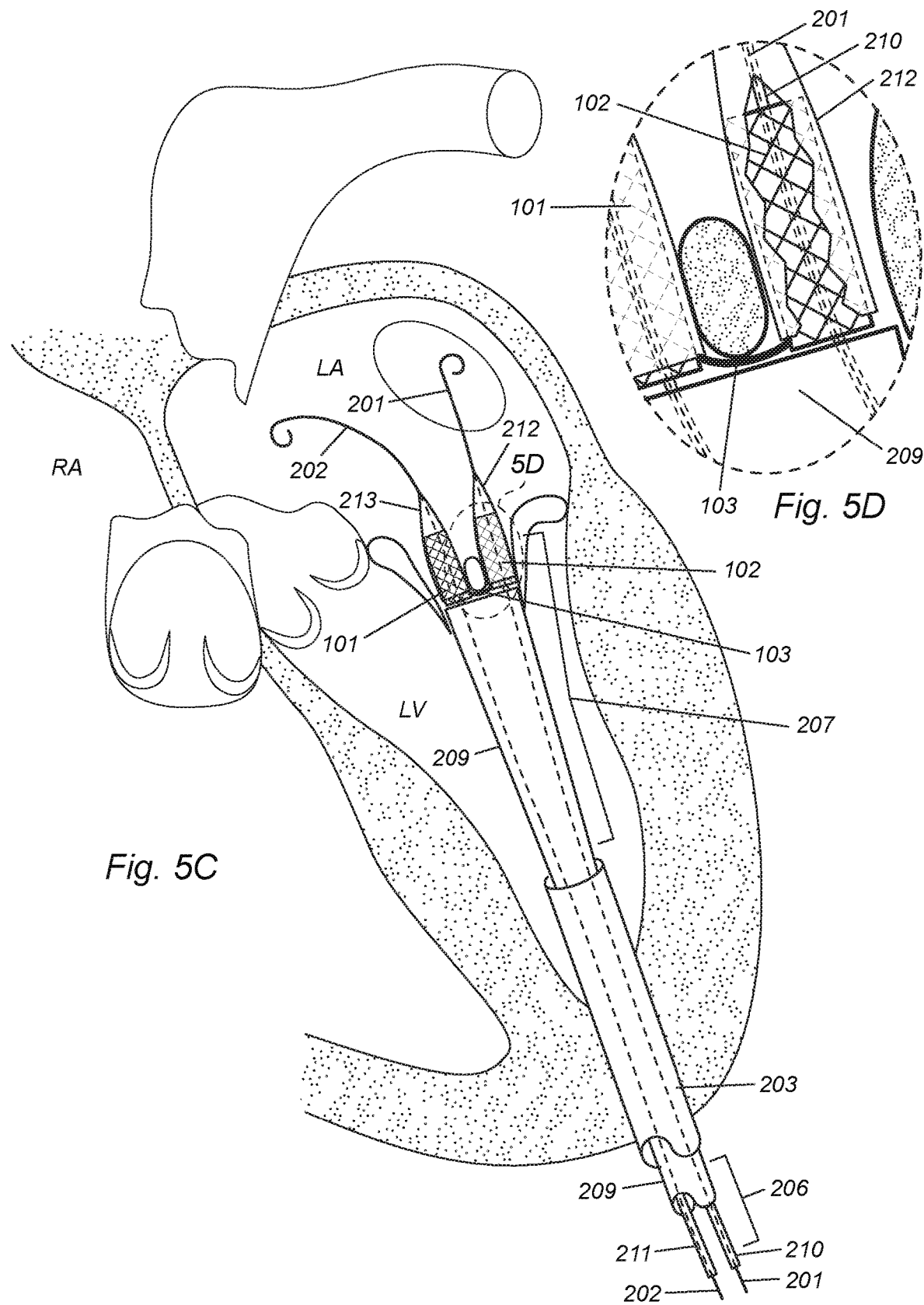

OPEN          OPEN

CLOSED       CLOSED

METHODS, DEVICES AND SYSTEMS FOR TRANSCATHETER MITRAL VALVE REPLACEMENT IN A DOUBLE-ORIFICE MITRAL VALVE

CROSS-REFERENCE TO RELATED APPLICATION

This application claims the benefit of priority under 35 U.S.C. § 120 as a continuation of U.S. application Ser. No. 15/101,362, filed Jun. 2, 2016, which is the National Phase of International Application No. PCT/US2014/069849, filed Dec. 11, 2014, which designated the U.S. and that International Application was published under PCT Article 21(2) in English, which also includes a claim of priority under 35 U.S.C. § 119(e) to U.S. provisional patent application No. 61/914,591 filed Dec. 11, 2013, the entirety of which is hereby incorporated by reference.

FIELD OF INVENTION

This invention relates to methods, devices and systems for transcatheter mitral valve replacement in a double-orifice mitral valve, which may be used to treat mitral valve diseases.

BACKGROUND OF THE INVENTION

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Valvular heart disease is characterized by damage to or a defect in one of the four heart valves: the mitral, aortic, tricuspid or pulmonary. The mitral and tricuspid valves control the flow of blood between the atria and the ventricles (the upper and lower chambers of the heart). The pulmonary valve controls the blood flow from the heart to the lungs, and the aortic valve governs blood flow between the heart and the aorta, and thereby to the blood vessels in the rest of the body. The mitral and aortic valves are most frequently affected by valvular heart disease.

Transcatheter valve therapies are one treatment option for patients. For example, transcatheter aortic valve replacement (TAVR—also known as TAVI or transcatheter aortic valve implantation) is a procedure for patients with severe symptomatic aortic stenosis (narrowing of the aortic valve opening) who are not candidates for traditional open chest surgery or are high-risk operable candidates. In these procedures, a replacement valve is inserted percutaneously using a catheter and implanted in the orifice of the native aortic valve. Replacement valves may be artificial (prosthetic valves) or made from animal tissue (bioprosthetic valves). The type of replacement valve selected depends on the patient's age, condition, and the specific valve affected.

The most common form of valvular heart disease is mitral regurgitation (MR), in which the two leaflets (anterior and posterior) of the mitral valve do not close properly when the heart pumps out blood. One procedure for MR is edge-to-edge leaflet repair. This procedure uses a suture, a percutaneous suture (e.g. Edwards' Mobius) or a clip (e.g. Abbott's Mitraclip) to bring the anterior and posterior leaflets together at their middle points, creating a "double-orifice" mitral valve. As a result, leaflet coaptation is re-established to reduce MR. Although often effective, this surgery still has a relatively high failure rate, due to either residual MR or, less commonly, increased transmitral flow gradients. Moreover, many patients are considered unsuitable for double orifice repair as there may be anatomical features that predict failure.

SUMMARY OF THE INVENTION

To treat subjects with mitral valve diseases (for example, MR patients who have had failed edge-to-edge leaflet repair), described herein is a double-orifice transcatheter mitral valve replacement (DO-TMVR) device. In some embodiments, this DO-TMVR device has a double-orifice structure that anchors to a patient's double-orifice mitral valve. A Y-shaped delivery system can be used to deliver the DO-TMVR device into the double-orifice mitral valve from the atrium or ventricle.

The following embodiments and aspects thereof are described and illustrated in conjunction with systems, compositions and methods which are meant to be exemplary and illustrative, not limiting in scope.

In various embodiments, provided herein is a device for transcatheter mitral valve replacement. The device comprises: a first replacement heart valve having a first atrial side and a first ventricular side; and a second replacement heart valve having a second atrial side and a second ventricular side.

In various embodiments, provided herein is a device for transcatheter mitral valve replacement. The device comprises: a first replacement heart valve having a first atrial side and a first ventricular side; a second replacement heart valve having a second atrial side and a second ventricular side; and a delivery catheter. In some embodiments, the delivery catheter has an inverted Y-shaped inflatable balloon at its distal end. In other embodiments, the delivery catheter has an inverted Y-shaped enclosing sheath at its distal end.

In various embodiments, provided herein is a device for transcatheter mitral valve replacement. The device comprises: a first replacement heart valve having a first atrial side and a first ventricular side; a second replacement heart valve having a second atrial side and a second ventricular side; and two guide wires, wherein a delivery catheter can be inserted over the two guide wires.

In various embodiments, provided herein is a device for transcatheter mitral valve replacement. The device comprises: a first replacement heart valve having a first atrial side and a first ventricular side; a second replacement heart valve having a second atrial side and a second ventricular side; and a sheath, wherein a delivery catheter can be inserted into the sheath.

In various embodiments, provided herein is a device for transcatheter mitral valve replacement. The device comprises: a first replacement heart valve having a first atrial side and a first ventricular side; a second replacement heart valve having a second atrial side and a second ventricular side; and a connector for connecting the two replacement valves, wherein the two replacement valves can be indirectly connected via the connector.

In an embodiment, the two replacement heart valves can be unconnected and anchored separately to the tissue formed by each of the two orifices of the double orifice. In some embodiments, if the residual regurgitation or stenosis is localized to one of the two orifices, a single prosthetic or bioprosthetic valve may be anchored to the tissue formed by that orifice, with the second orifice left without a prosthetic or bioprosthetic valve. In some embodiments, the two replacement heart valves can be connected on their atrial and/or ventricular sides. In accordance with the present invention, the two replacement heart valves can be connected prior to or after deployment of the device. As non-limiting examples, the two replacement heart valves may be indirectly connected via a hinge, click-and-lock system, tongue-and-groove system, interlocking structure, clasp, hook, ring, bolts, nut, screw, nail, fastener, magnet, mortise and/or tenon. In an embodiment, the two replacement heart valves may not be directly connected to each other; the two replacement heart valves may not extend from each other; the two replacement heart valves may not be held together by a frame or gasket; and/or no frame or gasket may surround both replacement heart valves.

In some embodiments, the two replacement valves can be prosthetic valves, bio-prosthetic valves, or a combination. In accordance with the present invention, the two replacement valves can be self-expandable valves, balloon expandable valves, a combination, or other suitable replacement valves. In some embodiments, the cross sections of the two replacement valves can be circles, ellipses, a combination, or other suitable shapes. In some embodiments, the cross sections of the two replacement valves can be two D shapes with their straight sides opposing each other.

In some embodiments, both or one of the two replacement valves can comprise stent frames made of iron, platinum, titanium, nickel, chromium, cobalt, magnesium, stainless steel, nitinol (nickel-titanium), nickel-chromium, cobalt-chromium, or platinum-iridium, or a combination thereof. In some embodiments, both or one of the two replacement valves comprises one, two, three, or more leaflets.

In various embodiments, provided herein is a method for transcatheter mitral valve replacement. The method comprises the following steps: (1) identifying a subject having a double-orifice mitral valve; (2) providing a device as described herein; and (3) delivering the device to the double-orifice mitral valve.

In various embodiments, provided herein is a method for treating residual MR after a double orifice repair or, less commonly, mitral stenosis (MS) after a double orifice repair. In various embodiments, the creation of a double orifice may facilitate the DO-TMVR in a patient that would normally be considered anatomically unsuitable for a double orifice repair due to a high anticipated risk of failure. The method comprises the following steps: (1) performing an edge-to-edge repair of a mitral valve in a subject, thereby creating a double-orifice mitral valve; (2) establishing that there is significant residual mitral valve disease; (3) providing a device as described herein; and (4) delivering the device to the double-orifice mitral valve.

In various embodiments, provided herein is a method for treating subjects with mitral valve diseases (for example, MR, residual MR, or MS). The method comprises the following steps: (1) performing an edge-to-edge repair of a mitral valve in a subject, thereby creating a double-orifice mitral valve; (2) assessing MR in the subject after the edge-to-edge repair; (3) if the edge-to-edge repair does not effectively treat MR and/or MS in the subject, providing a device as described herein; and (4) delivering the device to the double-orifice mitral valve. In accordance with the present invention, MR can be assessed with a variety of techniques and procedures known to one of ordinary skill in the art, including but not limited to, transthoracic and transesophageal echocardiography, angiography, MRI and transcatheter hemodynamic assessment. More details are described in Zoghbi et al. (Recommendations for evaluation of the severity of native valvular regurgitation with two-dimensional and Doppler echocardiography, American Society of Echocardiography, J Am Soc Echocardiogr., 2003 July; 16(7):777-802.), which is incorporated by reference herein in its entirety.

In accordance with the present invention, the device can be delivered transseptally or transapically. Still in accordance with the present invention, the subject can be a human or a mammal.

BRIEF DESCRIPTION OF FIGURES

Exemplary embodiments are illustrated in the referenced figures. It is intended that the embodiments and figures disclosed herein are to be considered illustrative rather than restrictive.

FIGS. 1A1, depicts a cross section of the heart including the left atrium and left ventricle. FIG. 1A2 depicts a cross section of the mitral valve with the anterior mitral leaflet and posterior mitral leaflet properly closed and sealed to prevent backflow. FIG. 1B1 depicts a cross section of the heart with mitral regurgitation. The arrows illustrate an example of back flow from the left ventricle to the left atrium through a leaky mitral valve. MR is often due to malcoaptation of the anterior and posterior leaflets of the mitral valve, or where the anterior and posterior leaflets do not fit together properly to form a seal. In a healthy mitral valve, normal coaptation prevents MR during systole (FIGS. 1A1 and 1A2). FIGS. 1B1, depicts a cross section of the heart including the left atrium and left ventricle. FIG. 1B2 depicts a cross section of the mistral valve. In a diseased mitral valve, malcoaptation results in jets of MR directed into the left atrium during systole (FIGS. 1B1 and 1B2). AML refers to anterior mitral leaflet; PML refers to posterior mitral leaflet; LA refers to left atrium; and LV refers to left ventricle.

FIG. 1C1 depicts a cross section of the heart including a leaking mitral valve. FIG. 1C2 depicts an example of a cross section of a mitral valve that has undergone an edge-to-edge repair procure. An edge-to-edge repair (for example, applying an Alfieri surgical stitch, (e.g., EDWARDS LIFE-SCIENCES' MOBIUS percutaneous stitch, or ABBOTT's MITRACLIP) involves the attachment of the center of the leaflets to each other as illustrated in the cross section of the valve shown in FIG. 1C2. This procedure brings the leaflets closer together and thereby reduces MR. However, this procedure may not completely address the MR, or patient may be excluded from having this procedure because of a high chance of failure. The present disclosed devices and methods capitalize on the partial apposition of the anterior and posterior mitral leaflets and use the connected tissue at their middle points as an anchor for a transcatheter mitral valve repair (TMVR) device, that is, a double-orifice TMVR device (DO-TMVR).

FIG. 2A depicts a cross section of a heart with a transseptal catheter 208 for delivery of a DO-TMVR device being advanced by entering through the femoral leg vein through to the right atrium. FIG. 2B depicts a first guide wire 201, a second guide wire 202, a sheath 203. FIG. 2C depicts a delivery catheter 204, and an inverted Y-shaped inflatable balloon at the delivery catheter's distal end. FIG. 2D also depicts a transseptal catheter 208, and two replacement valves 101 and 102 in a DO-TMVR device. Also illustrated is a connector 103 connecting replacement valve 101 to replacement valve 102. FIG. 2E also depicts a cross section of a heart with a transseptal catheter 208, and two replacement valves 101 and 102 in a DO-TMVR device.

FIG. 3A illustrates a cross section of the heart and the entry path for delivery of the DO-TMVR device. FIG. 3B illustrates the delivery catheter transapically inserted into the left ventricle and a first guide wire 201 a second guidewire 202, and a sheath 203. FIG. 3C illustrates the DO-TMVR device deployed from the catheter across the mitral valve. FIG. 3D illustrates the DO-TMVR device being further deployed in a cross section of the heart. FIG. 3E illustrates the DO-TMVR device being further deployed in a cross section of the heart.

FIG. 4A depicts the delivery of the catheter from the femoral vein through the right atrium and the delivery path through the septum. FIG. 4B illustrates the sheath 203 advanced through the septum of the heart into the left atrium. FIG. 4C depicts the DO-TMVR device being deployed in the mitral valve space. FIG. 4D is a cut-away view of a replacement valve 102 enclosed in a branch of the inverted Y-shaped enclosing sheath 207 (i.e., in the enclosing cap 212 placed at the distal end of the catheter 210). In the delivery catheter, two catheters 210 and 211 are inserted into a cover 209. The two replacement valves 101 and 102 are mounted near the distal ends of the two catheters 210 and 211. Further distal to the two replacement valves 101 and 102, two enclosing caps 212 and 213 are placed at the distal ends of the two catheters 210 and 211. The two enclosing caps 212 and 213 enclose the two replacement valves 101 and 102 to keep them compressed. FIG. 4E depicts the DO-TMVR device being deployed in the mitral valve space.

FIGS. 5A-E depict cross sectional views of the heart, in accordance with various embodiments, DO-TMVR devices comprising two self-expandable replacement valves, and a transapical procedure of deploying the DO-TMVR device. FIG. 5A depicts a cross sectional view of the heart. FIG. 5B depicts a sheath 203 transapically advanced into the left atrium. FIG. 5C illustrates the DO-TMVR device being deployed in the mitral valve. FIG. 5D is a cut-away view of a replacement valve 102 enclosed in a branch of the inverted Y-shaped enclosing sheath 207 (i.e., in the enclosing cap 212 placed at the distal end of the catheter 210). FIG. 5E illustrates the DO-TMVR device being deployed in the mitral valve.

FIG. 6A illustrates a perspective view of an embodiment of a DO-TMVR device for deployment transapically, including a connector 103 between the left valve 104 and right valve 105. As illustrated in FIG. 6A, for a DO-TMVR device to be deployed transapically, there may be a connector on the left ventricular side connecting the two replacement valves. FIG. 6B illustrates a perspective view of an embodiment of a DO-TMVR device for transseptical deployment, including a connector 103 between the left valve 104 and right valve 105. As illustrated in FIG. 6B, for a DO-TMVR device to be deployed transseptally, there may be a connecting means on the left atrial side connecting the two replacement valves. FIG. 6C illustrates a cross sectional view of an embodiment of a DO-TMVR device, including open leaflets 106. FIG. 6D illustrates a cross sectional view of an embodiment of a DO-TMVR device, including closed leaflets 106).

FIG. 7A illustrates a perspective view of an embodiment of a DO-TMVR device for deployment transapically, including a connector 103 between the left valve 104 and right valve 105. As illustrated in FIG. 7A, for a DO-TMVR device to be deployed transapically, there may be a connector 103 on the left ventricular side connecting the two replacement valves. FIG. 7B illustrates a perspective view of an embodiment of a DO-TMVR device for deployment transseptically, including a connector 103 between the left valve 104 and right valve 105. As illustrated in FIG. 7B, for a DO-TMVR device to be deployed transseptally, there may be a connector on the left atrial side connecting the two replacement valves. FIG. 7C illustrates a cross sectional view of an embodiment of a DO-TMVR device, including open leaflets 106. FIG. 7D illustrates a cross sectional view of an embodiment of a DO-TMVR device, including closed leaflets 106.

FIG. 8A illustrates an embodiment of a cross sectional view of a click-and-lock connection. FIG. 8B illustrates an embodiment of a cross sectional view of a click-and-lock connection. FIG. 8C illustrates a further embodiment of a cross sectional view of a click-and-lock connection.

DETAILED DESCRIPTION OF THE INVENTION

Figure 1D:
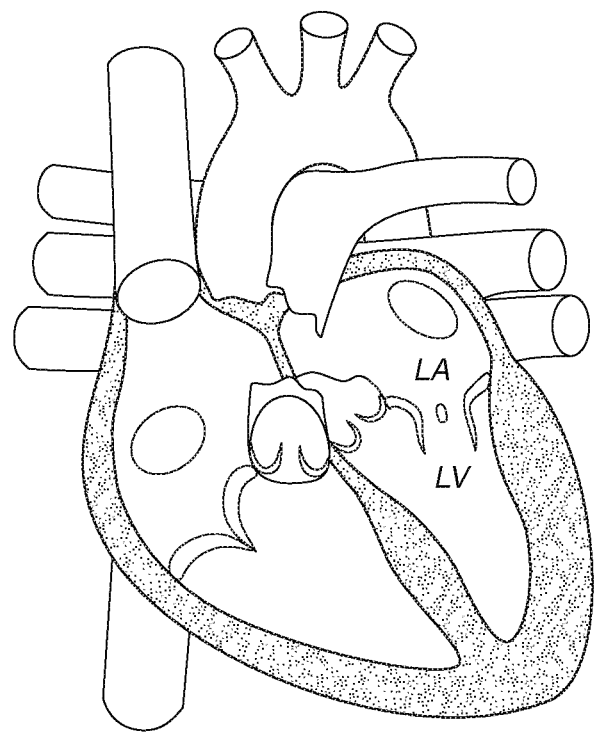
FIG. 1D depicts, in accordance with various embodiments, a perspective view of a deployed DO-TMVR comprising two replacement valves (101 and 102). In this non-limiting example, the two replacement valves (101 and 102) are both cylindrical.
Figure 1D:
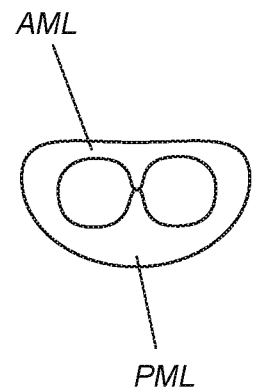
Figure 1D:
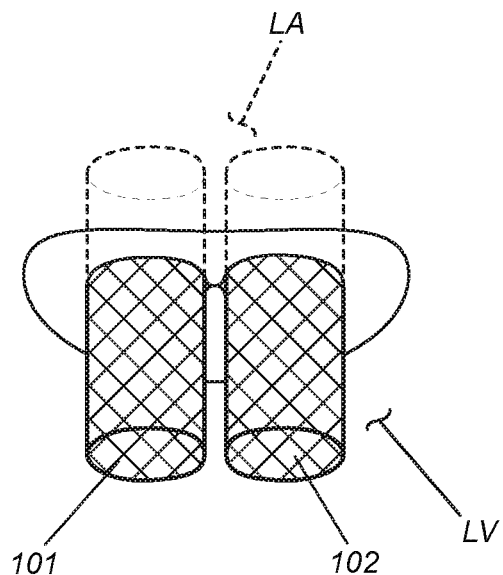
Figure 1E:
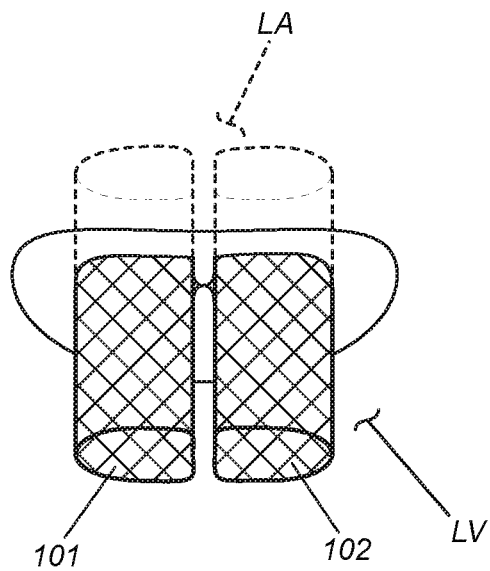
FIG. 1E depicts, in accordance with various embodiments, a perspective view of a DO-TMVR device comprising two replacement valves (101 and 102). In this non-limiting example, the two replacement valves (101 and 102) are shaped as two opposing D shapes.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., Dictionary of Microbiology and Molecular Biology 3rd ed., J. Wiley & Sons (New York, NY 2001); March, Advanced Organic Chemistry Reactions, Mechanisms and Structure 5th ed., J. Wiley & Sons (New York, NY 2001); and Sambrook and Russel, Molecular Cloning: A Laboratory Manual 3rd ed., Cold Spring Harbor Laboratory Press (Cold Spring Harbor, NY 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

Devices and Systems

Various embodiments of a device for a transcatheter mitral valve replacement. In some embodiments, the device comprises: a first replacement heart valve having a first atrial side and a first ventricular side; and a second replacement heart valve having a second atrial side and a second ventricular side.

In various embodiments, the two replacement heart valves are connected on their atrial and/or ventricular sides. In various embodiments, the two replacement heart valves are connected and various points between the two replacement heart valves including, halfway in between the ventricular and atrial sides, ⅓ of the way from the ventricular or atrial side or other suitable positions. In various embodiments, the two replacement heart valves are connected prior to or after deployment of the device. In various embodiments, the site of connecting the two replacement valves and the time of connecting the two replacement valves may depend on the access approach employed for device delivery (for instance, transseptal or transapical delivery).

In various embodiments, the two replacement heart valves are indirectly connected via a hinge, click-and-lock system, tongue-and-groove system, interlocking structure, clasp, hook, ring, bolts, nut, screw, nail, fastener, magnet, mortise and/or tenon. In various embodiments, the connector between the valves may dissolve over time. In some embodiments, the connector may include a tissue anchoring texture. In some embodiments, the connector may include a U shaped cross section other suitable cross section that conforms to the tissue to which it anchors at the center of the mitral valve. In various embodiments, the two replacement heart valves are not directly connected to each other and are individual deployed. In various embodiments, the two replacement heart valves do not extend from each other. In various embodiments, the two replacement heart valves are not hold together by a frame or gasket. In various embodiments, no frame or gasket surrounds both replacement heart valves.

In various embodiments, the first replacement heart valve is about 10-55 mm in height. In various embodiments, the second replacement heart valve is about 10-55 mm in height.

In various embodiments, the first replacement heart valve is about 10-55 mm in diameter. In various embodiments, the second replacement heart valve is about 10-55 mm in diameter. In some embodiments, either or both of the two replacement valves can have varying diameters along their longitudinal axes.

In various embodiments, the first replacement heart valve is a prosthetic valve or a bio-prosthetic valve. In various embodiments, the second replacement heart valve is a prosthetic valve or a bio-prosthetic valve. In various embodiments, the two replacement heart valves are prosthetic valves, bio-prosthetic valves, or combinations thereof. In accordance with the present invention, a prosthetic valve is made of purely artificial or non-biological materials, and a bioprosthetic valve is made of animal tissues alone or in combination with artificial or non-biological materials.

In various embodiments, the first replacement heart valve is self-expandable or balloon expandable. In various embodiments the second replacement heart valve is self-expandable or balloon expandable. An example of a self-expandable is the MEDTRONIC COREVALVE, which is constructed with a nitinol self-expanding valve stent frame and porcine pericardial leaflets. An example of a balloon-expandable valve includes, but is not limited to, the EDWARDS SAPIEN XT VALVE, which is constructed with a cobalt-chromium balloon-expandable valve stent frame and bovine pericardial leaflets.

In various embodiments, the cross section of the first and/or second replacement valve is a circle or ellipse, oval, or other suitable shapes that accommodate the mitral valve space. In various embodiments, the cross section of the two replacement valves are both D shapes with their straight sides opposing each other.

In various embodiments, the first replacement valves comprises stent frames made of iron, platinum, titanium, nickel, chromium, cobalt, magnesium, stainless steel, nitinol (nickel-titanium), nickel-chromium, cobalt-chromium, or platinum-iridium, or a combination thereof. In various embodiments, the second replacement valves comprises stent frames made of iron, platinum, titanium, nickel, chromium, cobalt, magnesium, stainless steel, nitinol (nickel-titanium), nickel-chromium, cobalt-chromium, or platinum-iridium, or a combination thereof.

In various embodiments, the first replacement valve comprises one, two, three, or more leaflets. In various embodiments, the second replacement valve comprises one, two, three, or more leaflets.

Various embodiments provide for a device for transcatheter mitral valve replacement. The device comprises: a first replacement heart valve having a first atrial side and a first ventricular side; a second replacement heart valve having a second atrial side and a second ventricular side; and a delivery catheter. In some embodiments, the delivery catheter has an inverted Y-shaped inflatable balloon at its distal end. In other embodiments, the delivery catheter has an inverted Y-shaped enclosing sheath at its distal end.

In accordance with the present invention, the delivery catheter can be comprised of one or more components. As one non-limiting example, the delivery catheter can be comprised of one inverted Y-shaped catheter with two inflatable balloons located on the two distal branches of the inverted Y-shaped catheter, and the first and second replacement valves of a DO-TMVR device are compressed and mounted over the two inflatable balloons. As another non-limiting example, the delivery catheter may be comprised of two inflatable balloon catheters enclosed in a cover sheath, with each catheter having an inflatable balloon located near or at its distal end. In some embodiments, the cover sheath encloses substantial portions of the two catheters, from their proximal ends to near the two inflatable balloons. In some embodiments, the distal portions of the two catheters, where the two inflatable balloons are located, are not enclosed by the cover sheath. In some embodiments, the delivery catheter, as a whole, resembles an inverted Y-shape; and the first and second replacement valves of a DO-TMVR device are compressed and mounted over the two inflatable balloons. As still another non-limiting example, the delivery catheter can be comprised of two catheters enclosed in a cover sheath. In some embodiments, the first and second replacement valves of a DO-TMVR device are compressed and mounted near the distal ends of the two catheters. In some embodiments, further distal to the two replacement valves, two enclosing caps are placed at the distal ends of the two catheters. In some embodiments, the two enclosing caps are distal to the two replacement valve. In some embodiments, the two enclosing caps enclose the two replacement valves to maintain them in compressed status.

In some embodiments, disclosed is a device for transcatheter mitral valve replacement. The device comprises: a first replacement heart valve having a first atrial side and a first ventricular side; a second replacement heart valve having a second atrial side and a second ventricular side; and two guide wires, wherein a delivery catheter can be inserted over the two guide wires.

In some embodiments, disclosed is a device for transcatheter mitral valve replacement. The device comprises: a first replacement heart valve having a first atrial side and a first ventricular side; a second replacement heart valve having a second atrial side and a second ventricular side, and a sheath, wherein a delivery catheter can be inserted into the sheath.

In some embodiments, disclosed is a device for transcatheter mitral valve replacement. The device comprises: a first replacement heart valve having a first atrial side and a first ventricular side; a second replacement heart valve having a second atrial side and a second ventricular side; and a connecting means for connecting the two replacement valves, wherein the two replacement valves can be indirectly connected via the connecting means. In some embodiments, disclosed is a device with two or more connectors. In some embodiments, the connector can be located on the left atrial side, the left ventricular side, or on both left atrial and left ventricular sides. The connector may be connected prior to or after deployment of a DO-TMVR device. Various connectors can be used to connect the two replacement valves. Examples of the connectors include but are not limited to a hinge, click-and-lock system, tongue-and-groove system, interlocking structure, clasp, hook, ring, bolts, nut, screw, nail, fastener, magnet, mortise and/or tenon. Other examples may be found in US 20100185275 A1 and U.S. Pat. No. 5,250,071, which are incorporated herein by reference as a whole. In some embodiments, the connector comprises two or more components, for example, a click-and-lock system or a tongue-and-groove system. In other embodiments, the connector comprises only one component, for example, a bridge, string, wire, beam or joist.

Suitable examples of guide wires, sheaths, and catheters that may be utilized with the presently disclosed devices, systems and methods described herein will be apparent to a person of skill in the art. Examples of suitable guidewires, sheaths and catheters are disclosed in for example, Ye et al. (Transapical aortic valve implantation in humans. Ye J, Cheung A, Lichtenstein S V, Carere R G, Thompson C R, Pasupati S, Webb J G. J Thorac Cardiovasc Surg. 2006 May; 131(5):1194-6) and Lichtenstein et al. (Transapical transcatheter aortic valve implantation in humans: initial clinical experience. Lichtenstein S V, Cheung A, Ye J, Thompson C R, Carere R G, Pasupati S, Webb J G. Circulation. 2006 Aug. 8; 114 (6):591-6. Epub 2006 Jul. 31), the contents of each of which are herein incorporated by reference.

Materials which may be used to construct the device comprising replacement heart valves are well known in the art, for example as described in U.S. Publication No. US2011/0319989, which is incorporated by reference herein in its entirety.

Methods

Disclosed are various embodiments of a method for transcatheter mitral valve replacement. The method comprises the following steps: (1) identifying a subject having a double-orifice mitral valve; (2) providing a device as described above; and (3) delivering the device to the double-orifice mitral valve.

Disclosed are various embodiments for a method for treating mitral valve diseases (such as MR, residual MR, or MS). The method comprises the following steps: (1) performing an edge-to-edge repair of a mitral valve in a subject, thereby creating a double-orifice mitral valve; (2) providing a device as described above; and (3) delivering the device to the double-orifice mitral valve.

Disclosed are various embodiments for a method for treating mitral valve diseases (such as MR, residual MR, or MS). The method comprises the following steps: (1) performing an edge-to-edge repair of a mitral valve in a subject, thereby creating a double-orifice mitral valve; (2) assessing MR or MS in the subject after the edge-to-edge repair; (3) if the edge-to-edge repair does not effectively treat MR or MS in the subject, providing a device as described above; and (4) delivering the device to the double-orifice mitral valve.

In various embodiments, the device is delivered transseptally or transapically. In various embodiments, the subject is a human. In various embodiments, the subject is a mammal.

In various embodiments, the devices, systems and methods described herein are configured for humans. One of skill in the art would readily appreciate that the devices, systems and methods described herein could be customized for use in almost any mammal in which a heart valve may be replaced. "Mammal" as used herein refers to any member of the class Mammalia, including but not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. In certain embodiments, the mammal is a human subject. The term does not denote a particular age or sex. Thus, adult, newborn, fetuses, male or female mammalian heart surgery is within the scope of this disclosure.

Also in accordance with the present invention, as regular TMVR is a known surgical procedure, one of ordinary skill in the art would readily recognize that the method could involve other additional steps, which are not described in details here. These additional steps include, but are not limited to, anesthesia, sterilization, heparinization, accessing the patient's heart via various routes such as femoral, transseptal, transaortic and transapical approaches, ventricular pacing, stitching of the access site or percutaneous femoral closure. For example, more information on these procedures are described in Masson et al. (Percutaneous treatment of mitral regurgitation; Circ Cardiovasc Interv. 2009 April; 2(2):140-6.) and Chiam et al. (Percutaneous transcatheter mitral valve repair: a classification of the technology; JACC Cardiovasc Interv. 2011 Jan. 4(1):1-13.), each of which is incorporated herein by reference in its entirety.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Repair of the mitral valve using the edge-to-edge technique can be performed surgically (e.g., Alfieri stitch) or percutaneously (e.g., EDWARDS LIFESCIENCES' MOBIUS and ABBOTT's MITRACLIP). It involves joining or bringing together the middle of the anterior and posterior leaflets of the mitral valve, thereby making a single orifice a double orifice. This is intended to reduce the gap between the two leaflets that can occur during systole in pathological states that often causes MR.

Although edge-to-edge repair can achieve excellent results in MR, it has strict anatomical criteria for case selection that limits the number of patients that qualify for it. Moreover, the failure rate of this procedure remains relatively high. Currently, failure of edge-to-edge repair is addressed either by medical therapy in inoperable patients or surgical revision in those who are operable. However, there is presently no percutaneous option for such patients.

In some embodiments, the presently disclosed DO-TMVR methods, devices, and systems solve these problems. For example, implantation of a DO-TMVR can be used to treat patients who have had a failed edge-to-edge mitral valve repair procedure for severe mitral regurgitation (MR).

In some embodiments, the design of DO-TMVR utilizes the double orifice of the mitral valve as a reliable tissue anchor and to provide a seal around the device. Also, if treatment of MR with a DO-TMVR is an available option, then edge-to-edge repair procedures, rather than having strict anatomical criteria for case selection, could be attempted in a broader group of patients. This is because if an edge-to-edge repair failed, DO-TMVR could still be employed to remedy the defective valve.

Implantation of the presently disclosed DO-TMVR device may be performed antegradely (from femoral vein to RA to transseptal puncture to LA to mitral valve) or retrogradely (from LV apex to LV to mitral valve). In some embodiments, the DO-TMVR device includes two replacement valves that are mounted on a delivery catheter. The two replacement valves may be separate or connected, and may be deployed separately or together. The two replacement valves may contain cylindrical stent structures and may each carry one, two, three or more leaflets. The leaflets may be biological or artificial. The stent structures may be made of nitinol or other alloys (e.g., stainless steel, cobalt-chromium, and platinum-iridium). The two replacement valves may be self-expandable or balloon-expandable. As illustrated in FIG. 1D, each of the two replacement valves may be implanted into each of the two orifices of the double-orifice mitral valve created by an edge-to-edge repair.

Implantation of the presently disclosed DO-TMVR device could be performed during an edge-to-edge repair procedure, or preferably at a later time, when scar tissue has formed over the edge-to-edge repair. Waiting until scar tissue has formed may ensure that there is a more reliable tissue scaffold for an anchor, and may also prevent scar tissue formation from interfering with the valve fit or operation.

Example 2 Transseptal Balloon-Expandable DO-TMVR

Figures 2A, 2B:
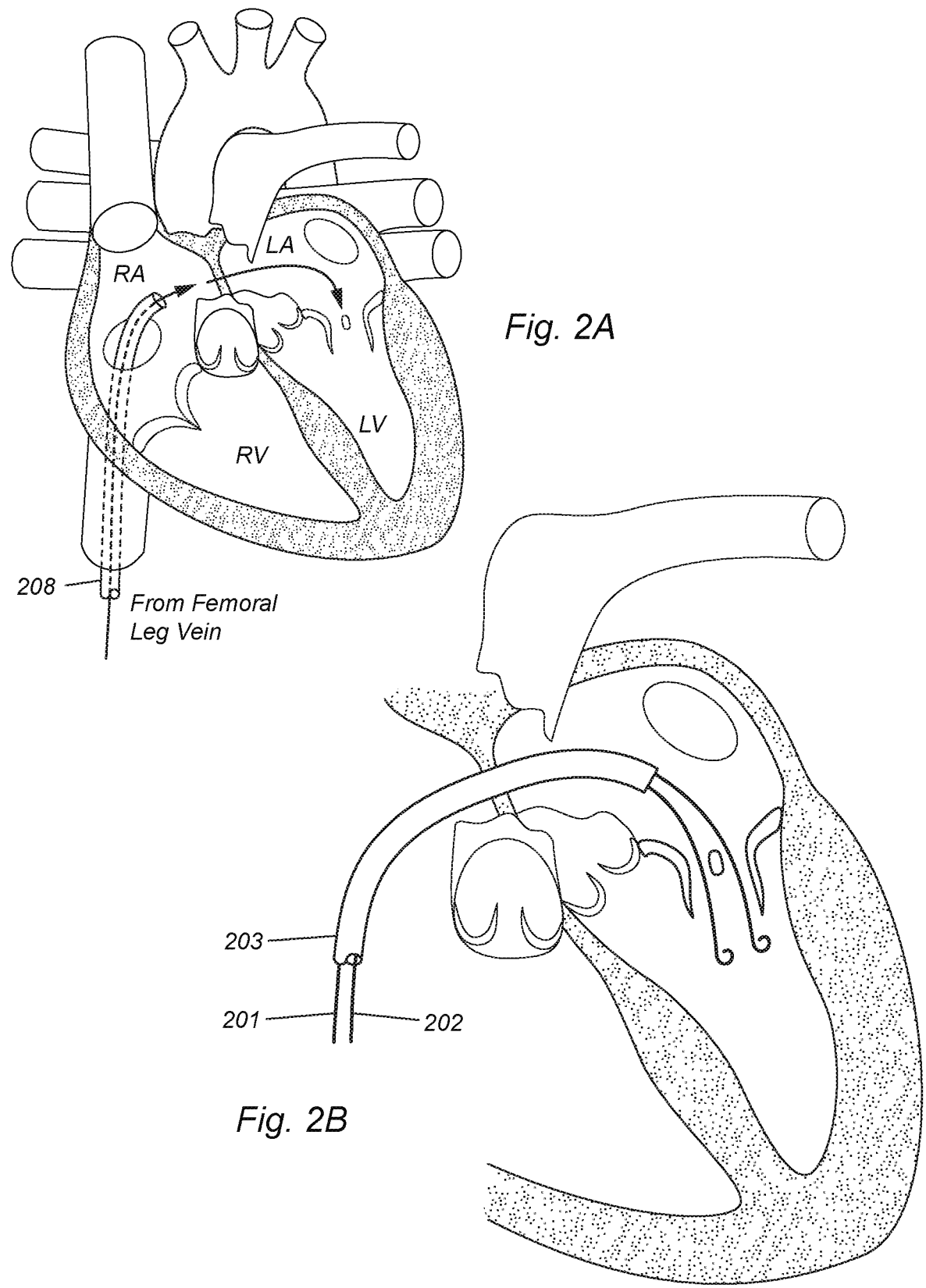
FIGS. 2A-E depict cross sections of the heart, in accordance with various embodiments, a DO-TMVR device comprising two balloon-expandable replacement valves and a transseptal procedure of deploying the DO-TMVR device and a method of surgically implanting the DO-TMVR device.

FIGS. 2A-E illustrate an example of a transseptal DO-TMVR procedure using one of the presently disclosed devices. In some embodiments, after induction of anesthesia and sterile preparation, an incision is made in the femoral leg vein. Alternatively, percutaneous femoral access is performed with or without pre-closure. In some embodiments, a transseptal catheter 208 is advanced over a wire and inserted to the right atrium from the femoral leg vein, via the inferior vena cava (IVC), to the right atrium (RA) and placed in close proximity to the inter-atrial septum. Then, the guidewire may be removed. As illustrated in FIG. 2A, in some embodiments, a transseptal puncture needle (shown as an arrow in FIG. 2A) may then be advanced through the transseptal catheter. The transseptal puncture needle may then be utilized to puncture the heart septum from RA to left atrium (LA). Then, the transseptal catheter may then be inserted over the transseptal needle through the puncture of the interatrial septum. The transseptal puncture needle may then be withdrawn via the transseptal catheter out of the patient's body, leaving only the transseptal catheter in the left atrium. Following this, the transseptal catheter may be exchanged for a sheath 203 (which may be of 12 Fr-24 Fr) by wire exchange. As illustrated in FIG. 2B, two guide wires 201 and 202 (which may be of 110-260 cm length and 0.018"-0.038" caliber) may then be inserted into the sheath 203 and further across each orifice of the double-orifice mitral valve.

Figure 2C:
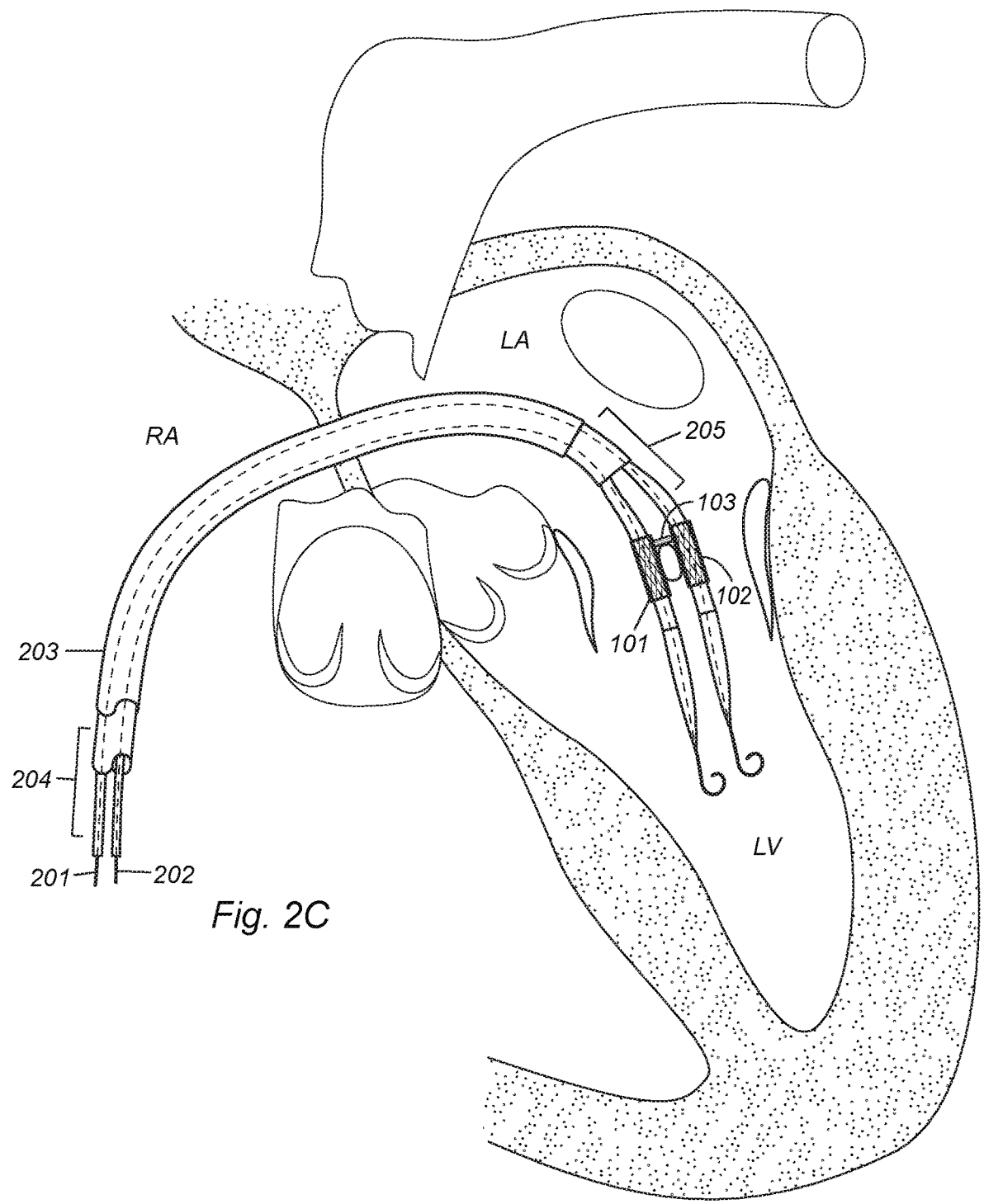
Figure 2D:
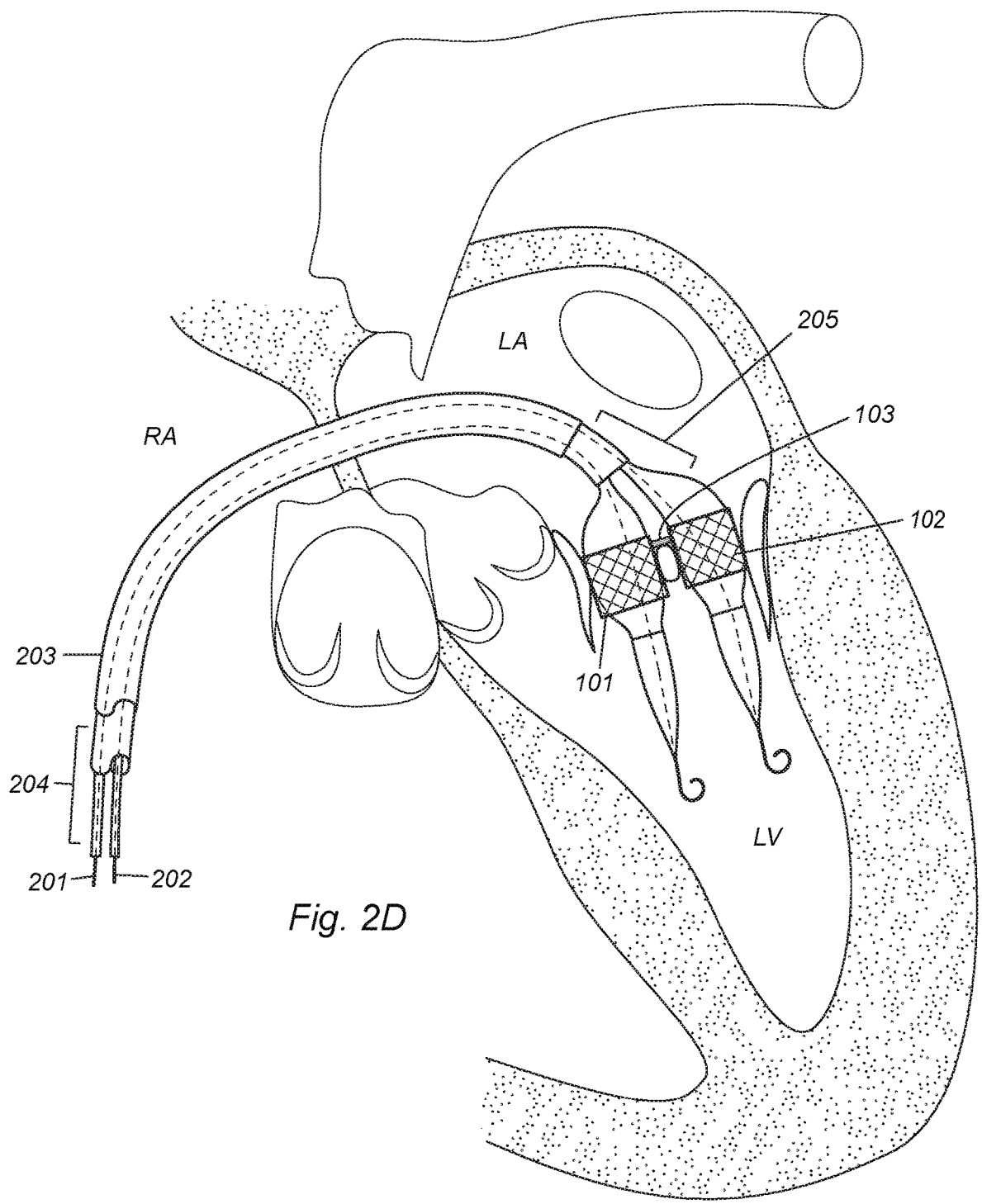
Figure 2E:
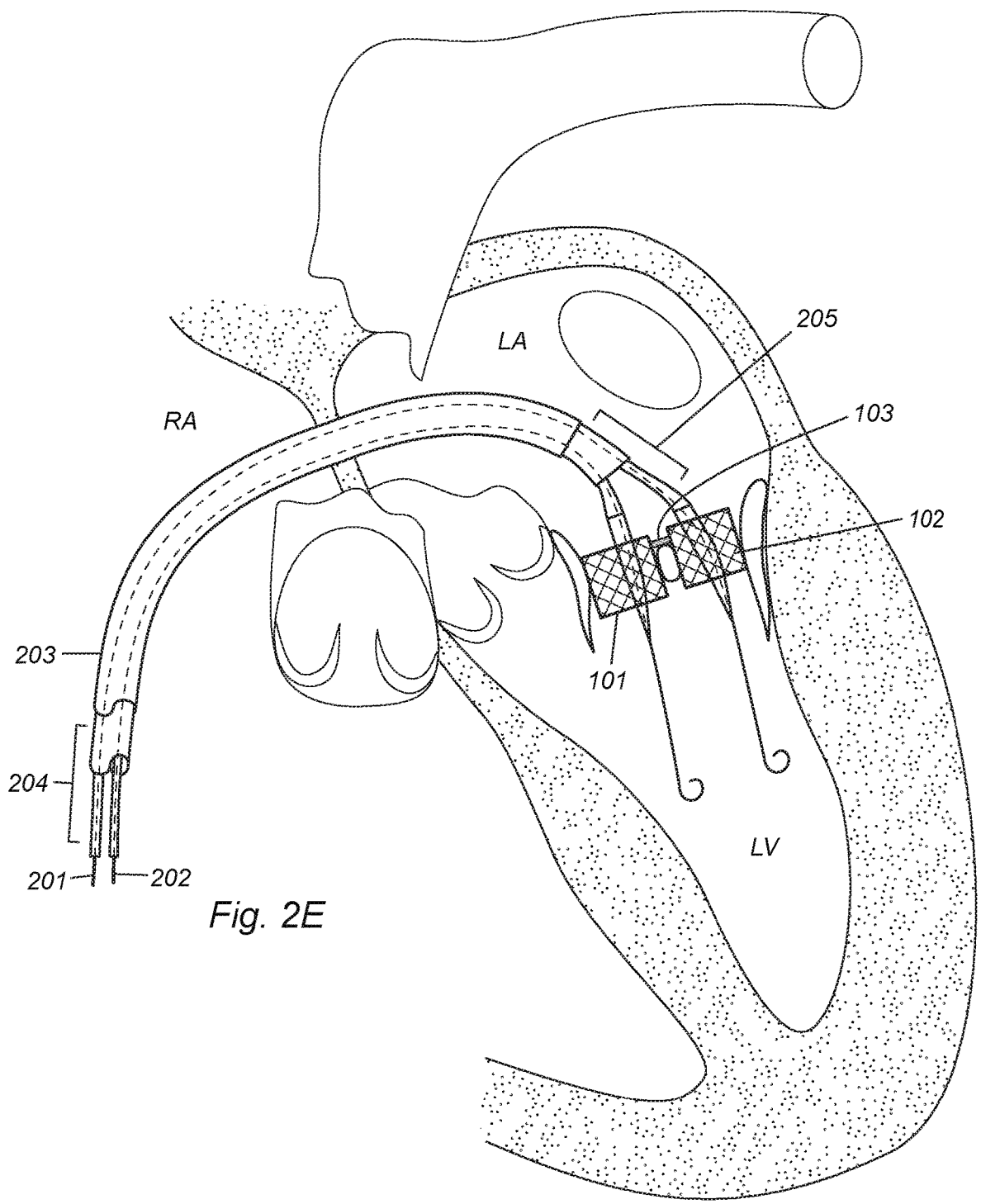

In some embodiments, a delivery catheter 204 (which may be 12 Fr-24 Fr) having an inverted Y-shaped inflatable balloon 205 at its distal end may then be inserted over the two guide wires (201 and 202) and into the sheath 203. The first and second replacement valves (101 and 102) of a DO-TMVR device may then be mounted on the two end branches of the inverted Y-shaped inflatable balloon 205. In this example, the two replacement valves (101 and 102) are connected via a connector 103 such as a hinge prior to delivery. In some embodiments, the two replacement valves (101 and 102) are connected via a connector 103 such as a hinge during the manufacturing process and are loaded onto the delivery catheter 204 as two connected valves. In some embodiments, prior to delivery and while loaded into the delivery catheter 204 the two replacement valves (101 and 102) are in compressed state inside the catheter and an inverted Y-shaped inflatable balloon is deflated. As illustrated in FIG. 2C, the delivery catheter 204 is guided to the double-orifice mitral valve so that a replacement valve (101 and/or 102) is placed in each orifice. Then, the inverted Y-shaped inflatable balloon may be inflated to expand the two replacement valves (101 and 102). As illustrated in FIG. 2D, as a result, a seal is formed between the two replacement valves (101 and 102) and the double-orifice mitral valve, and on the atrial side, the connector 103 such as a hinge is anchored or sits on top of the middle portion of the anterior and posterior leaflets that has been surgically connected. As illustrated in FIG. 2E, the inverted Y-shaped inflatable balloon may then be deflated and the delivery catheter may be withdrawn via the sheath out of the patient's body. Following, the two guide wires (201 and 202) may be withdrawn via the sheath 203 out of the patient's body. Additional standard steps that may be performed during the procedure may include heparinization and closure of the femoral vein either by manual compression, suture-mediated pre-closure or surgical closure. The procedure may be performed with local anesthesia with conscious sedation or general anesthesia. Heparinization may be reversed at the end of the procedure by administration of protamine. Heparin intolerant individuals may be anticoagulated during the procedure using direct thrombin inhibitors.

Example 3 Transapical Balloon-Expandable DO-TMVR

FIGS. 3A-3E illustrate a further example of an implantation procedure utilizing a transapical DO-TMVR device. After induction of anesthesia, and sterile preparation, an apical incision may be performed by a standard procedure as described in for example, Lichtenstein et al. Transapical transcatheter aortic valve implantation in humans: initial clinical experience. Circulation. 2006 Aug. 8; 114(6):591-6. Epub 2006 Jul. 31, which is incorporated by reference herein in its entirety.

In some embodiments, the apex of the heart may be exposed for the surgical approach or punctured with a needle directly under ultrasound guidance for a percutaneous approach. For a surgical approach, pledgeted sutures may be placed in a ring over the left ventricle (LV) apical surface. An example of a percutaneous approach is described in Dudiy et al. Percutaneous closure of left ventricular pseudoaneurysm, Circ Cardiovasc Interv. 2011 August; 4(4): 322-6. Epub 2011 Jul. 26, which is incorporated by reference herein in its entirety.

Figure 3A:
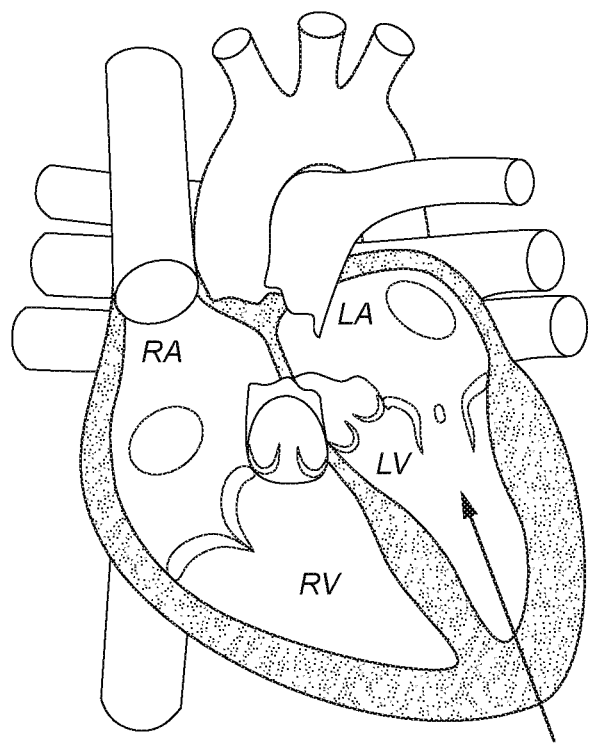
FIGS. 3A-E depict, in accordance with various embodiments, a cross section of a heart, a DO-TMVR device comprising two balloon-expandable replacement valves, and a transapical procedure of deploying the DO-TMVR device.
Figure 3B:
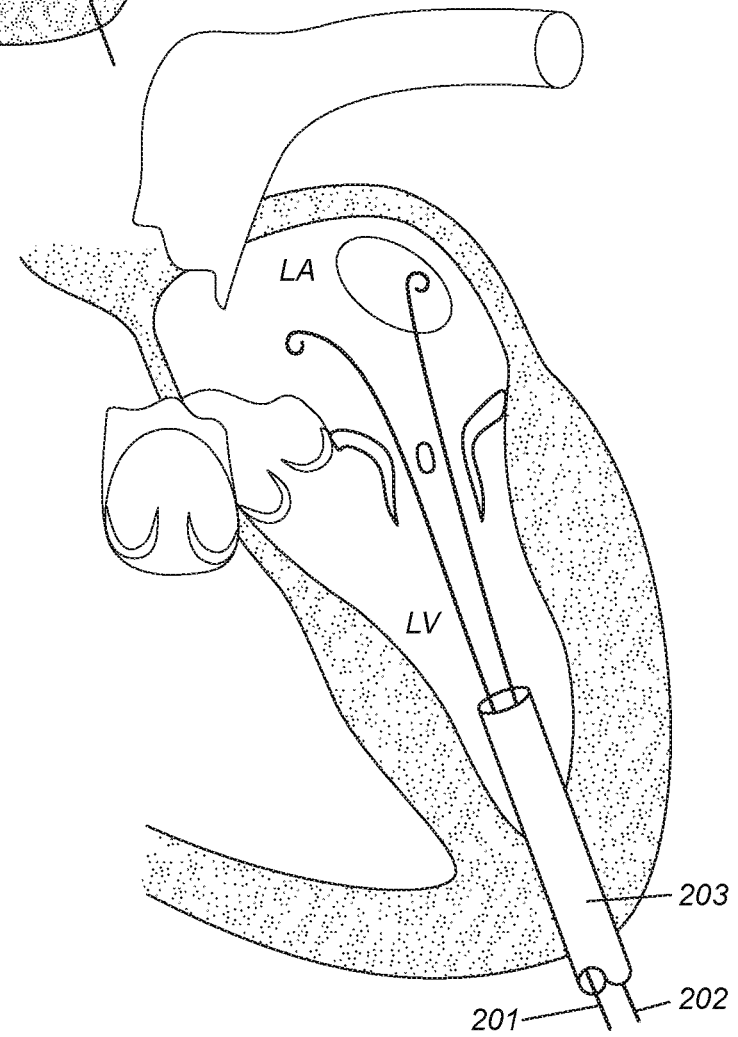

FIG. 3A illustrates a needle of gauge 12-16, or other suitable gauges, that may be utilized to puncture the LV apex. In some embodiments, after the puncture of the LV apex, a first guide wire 201 of caliber 0.014"-0.038" may be inserted through the needle, into LV, through one of the two orifices of the double-orifice mitral valve, and into LA. Then, the needle may be withdrawn. A sheath of size 4-7 Fr is inserted, and exchanged over a 0.035" or 0.038" wire to another sheath 203 of size 12-24 Fr, which is inserted over the guide wire (201 and/or 202) into LV. FIG. 3B illustrates a second guide wire 202 being inserted into the sheath 203, into LV, through the other of the two orifices of the double-orifice mitral valve and into LA.

Figure 3C:
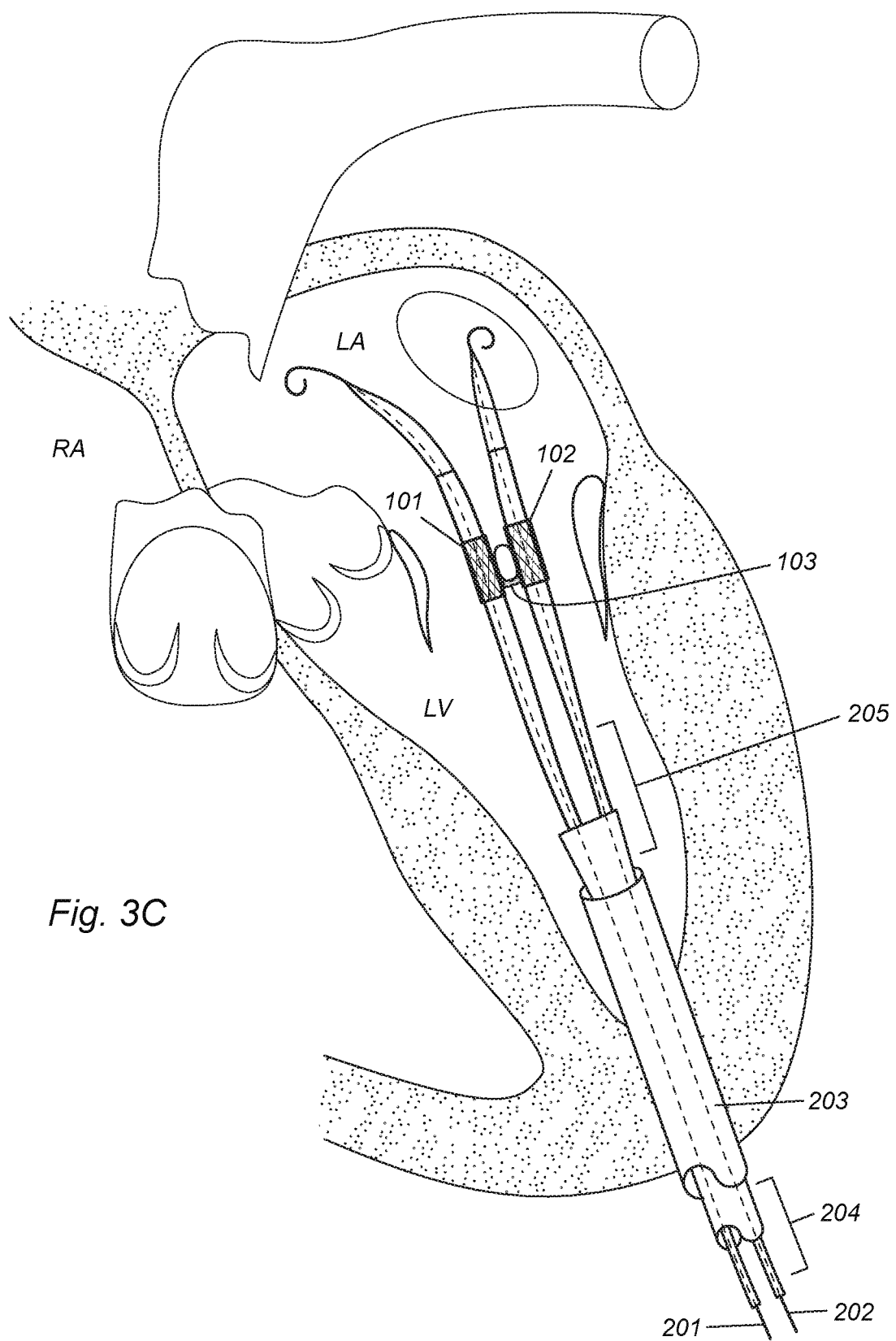
Figure 3D:
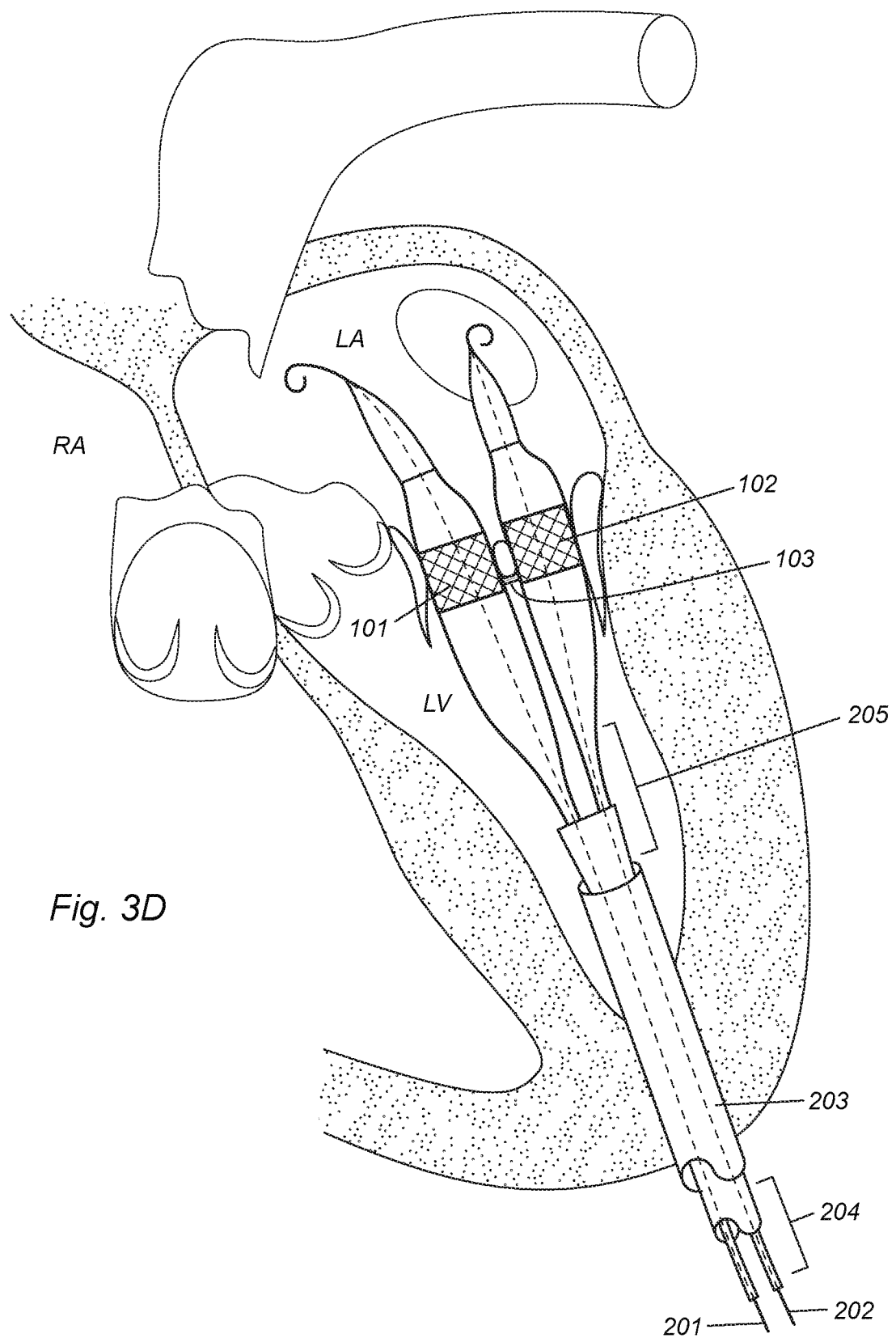
Figure 3E:
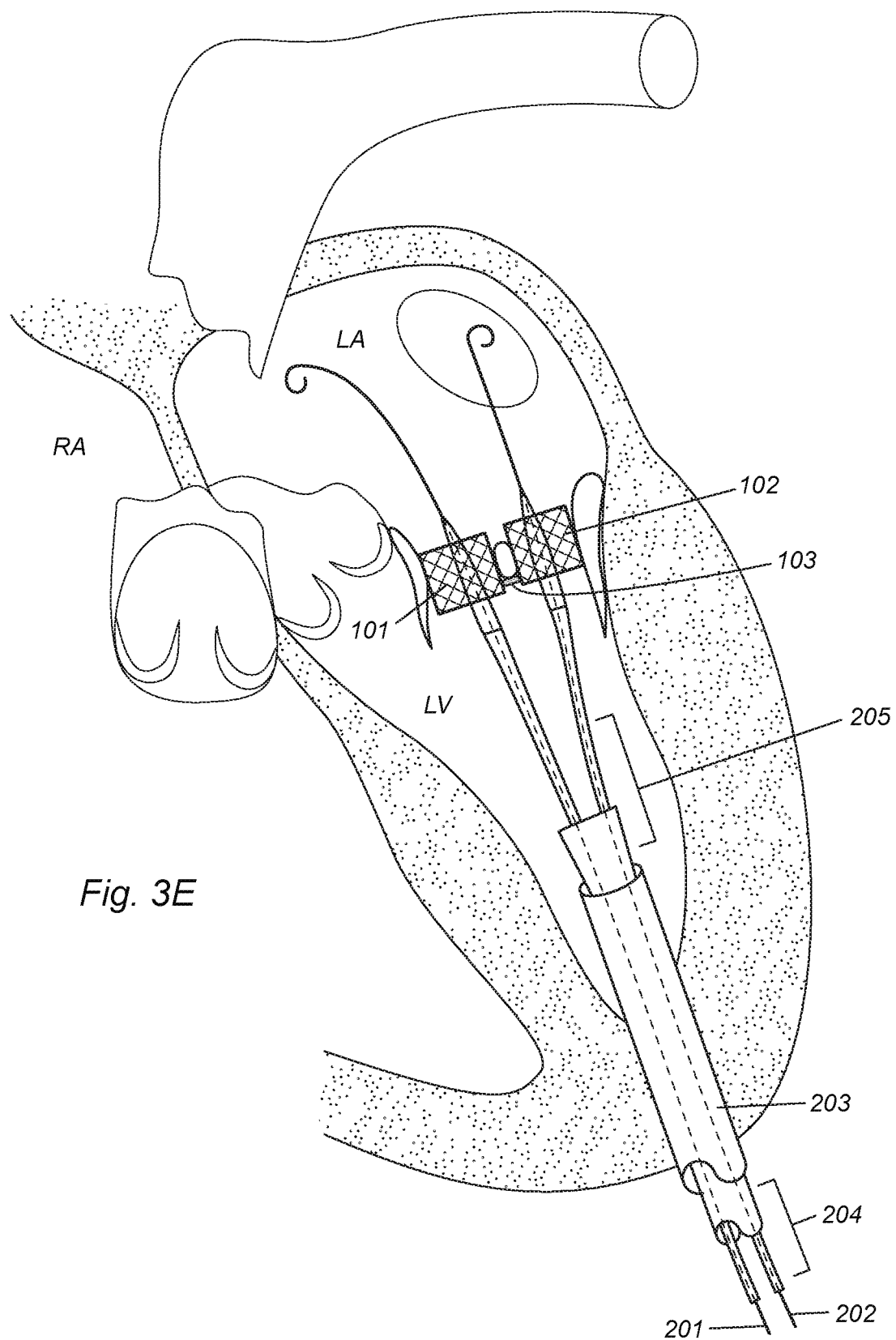

Next, a delivery catheter 204 (which may be 12 Fr-24 Fr) having an inverted Y-shaped inflatable balloon 205 at its distal end may be inserted over the two guide wires (201 and 202) and into the sheath 203. Then, the first and second replacement valves (101 and 102) of DO-TMVR device may be mounted on the two end branches of the inverted Y-shaped inflatable balloon 205. In this example, the two replacement valves (101 and 102) may be connected via a connector 103 such as a hinge prior to delivery. The two replacement valves (101 and 102) are already connected via a connector 103 such as a hinge during the manufacturing process and are loaded onto the delivery catheter 204 as two connected valves. While loaded into the delivery catheter 204, the two replacement valves (101 and 102) are in compressed status and the inverted Y-shaped inflatable balloon is deflated. FIG. 3C illustrates the delivery catheter 204 being guided to the double-orifice mitral valve so that a replacement valve (101 and 102) is placed in each orifice. The inverted Y-shaped inflatable balloon may then be inflated to expand the two replacement valves (101 and 102). As illustrated in FIG. 3D, after inflation of the valves (101 and 102), a seal is formed between the two replacement valves (101 and 102) and the double-orifice mitral valve, and on the ventricular side, the connector 103 such as a hinge may be anchored below the connected middle of the anterior and posterior leaflets 106. As illustrated in FIG. 3E, the inverted Y-shaped inflatable balloon may then be deflated and the delivery catheter 204 may then be withdrawn via the sheath 203 and out of the patient's body. Then, the two guide wires (201 and 202) may be withdrawn via the sheath 203 out of the patient's body, and then the sheath 203 itself is withdrawn out of the patient's body. During the procedure, additional standard steps may be performed such as heparinization and/or closure of the apex either surgically or utilizing a transcatheter approach with an Amplatzer or dedicated closure device. The procedure is performed under general anesthesia and the patient is generally woken up immediately after the procedure. Heparinization may be reversed at the end of the procedure by administration of protamine. Heparin intolerant individuals may be anticoagulated during the procedure using direct thrombin inhibitors.

Example 4 Transseptal Self-Expandable DO-TMVR

Figure 4A:
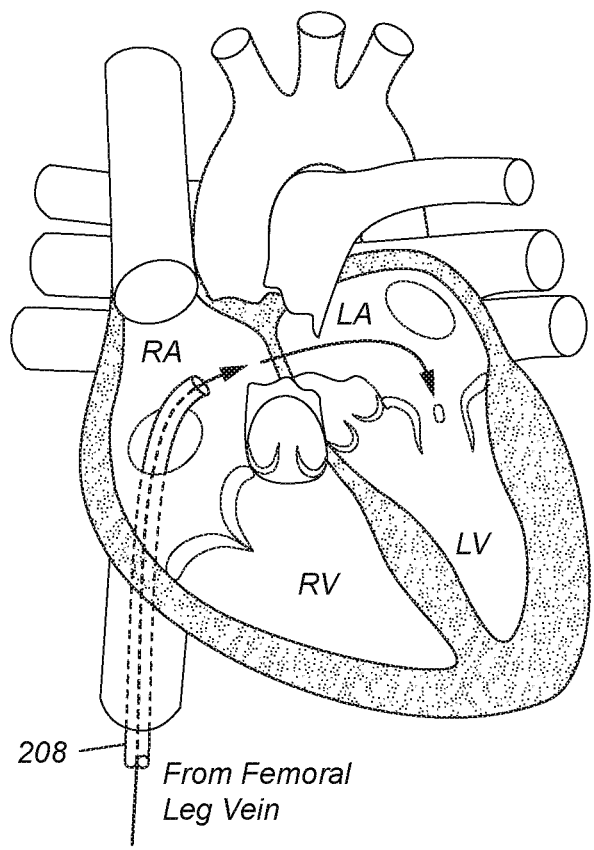
FIGS. 4A-E depict, a cross section of a heart in accordance with various embodiments, a DO-TMVR device comprising two self-expandable replacement valves, and a transseptal procedure of deploying the DO-TMVR device.
Figure 4B:
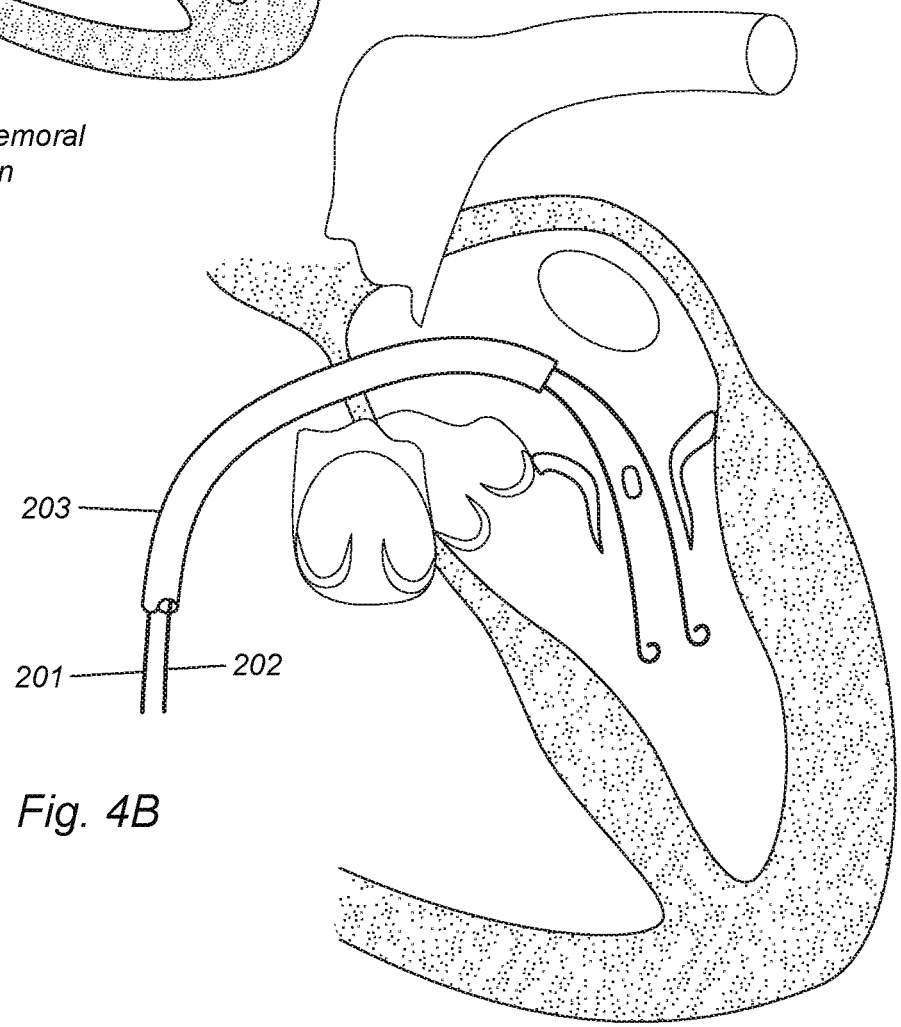

FIGS. 4A-4D illustrate an example of a transseptal implantation procedure for a DO-TMVR a device as disclosed herein. After induction of anesthesia, and sterile preparation, an incision is performed at the femoral leg vein. Alternatively, percutaneous femoral access may be performed with or without pre-closure. A transseptal catheter 208 may then be advanced over a wire 201 and/or 202 and inserted to the right atrium from the femoral leg vein, via inferior vena cava (IVC), to the right atrium (RA) and placed close to the inter-atrial septum. The wire 201 and/or 202 may then be removed. As illustrated in FIG. 4A, a transseptal puncture needle may then be advanced through the transseptal catheter. In some embodiments, the transseptal puncture needle may be utilized to puncture the heart septum from RA to left atrium (LA). After puncture of the heart septum, the transseptal catheter may then be inserted over the transseptal needle through the puncture of the septum. The transseptal puncture needle may then be withdrawn via the transseptal catheter out of the patient's body, leaving only the transseptal catheter in the left atrium. The transseptal catheter 208 may then be exchanged for a sheath 203 (which may be of 12 Fr-24 Fr) by wire exchange. As illustrated in FIG. 4B, two guide wires 201 and 202 (which may be of 110-260 cm length and 0.018"-0.038" caliber) may then be inserted into the sheath 203 and further across each orifice of the double-orifice mitral valve.

Figure 4D:
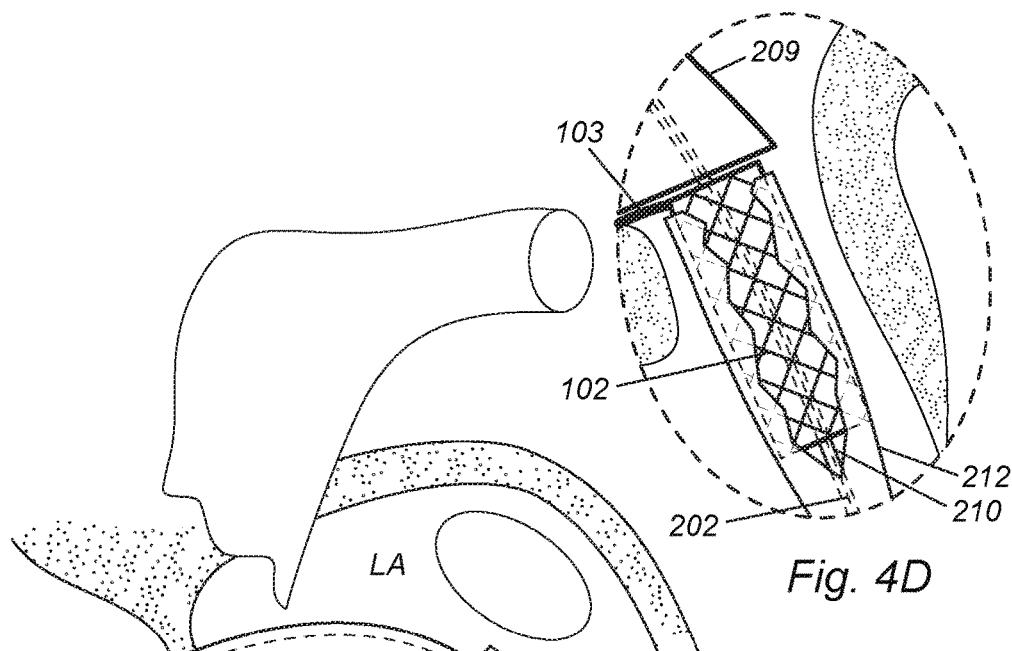
Figure 4C:
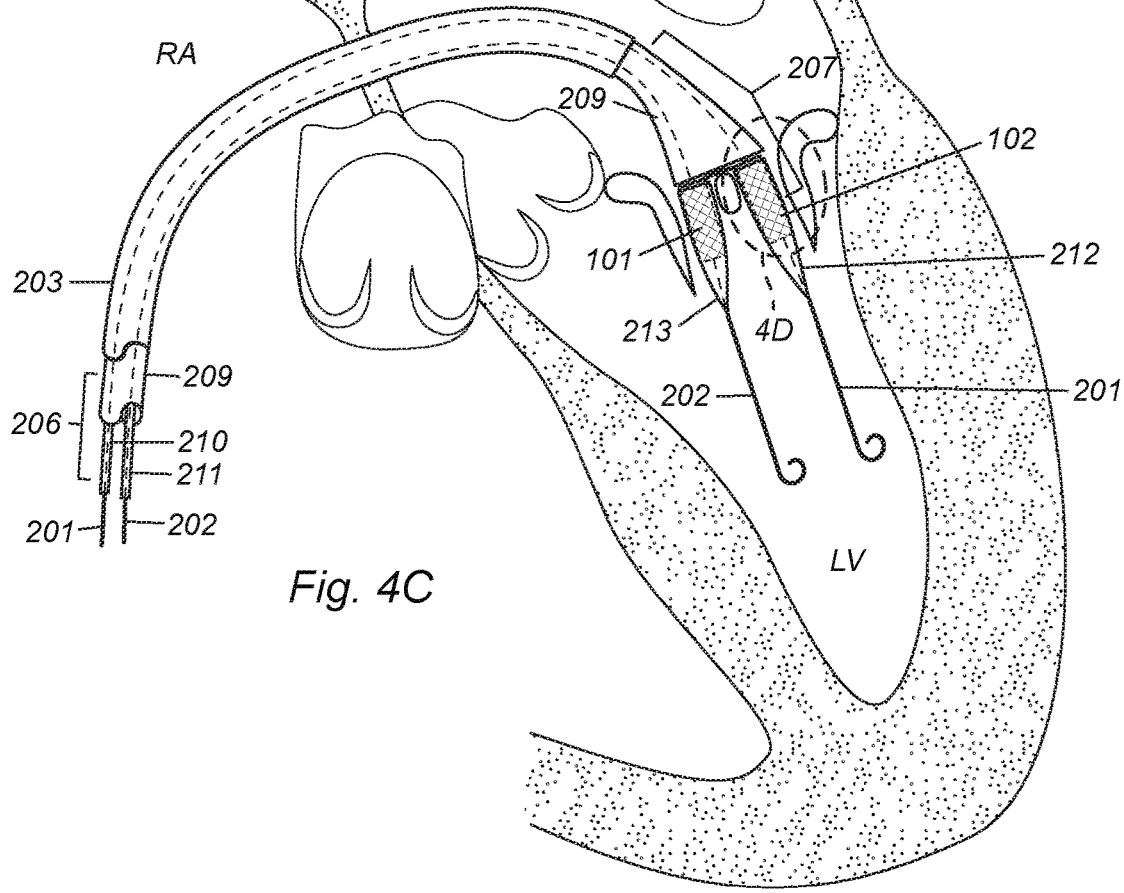
Figure 4E:
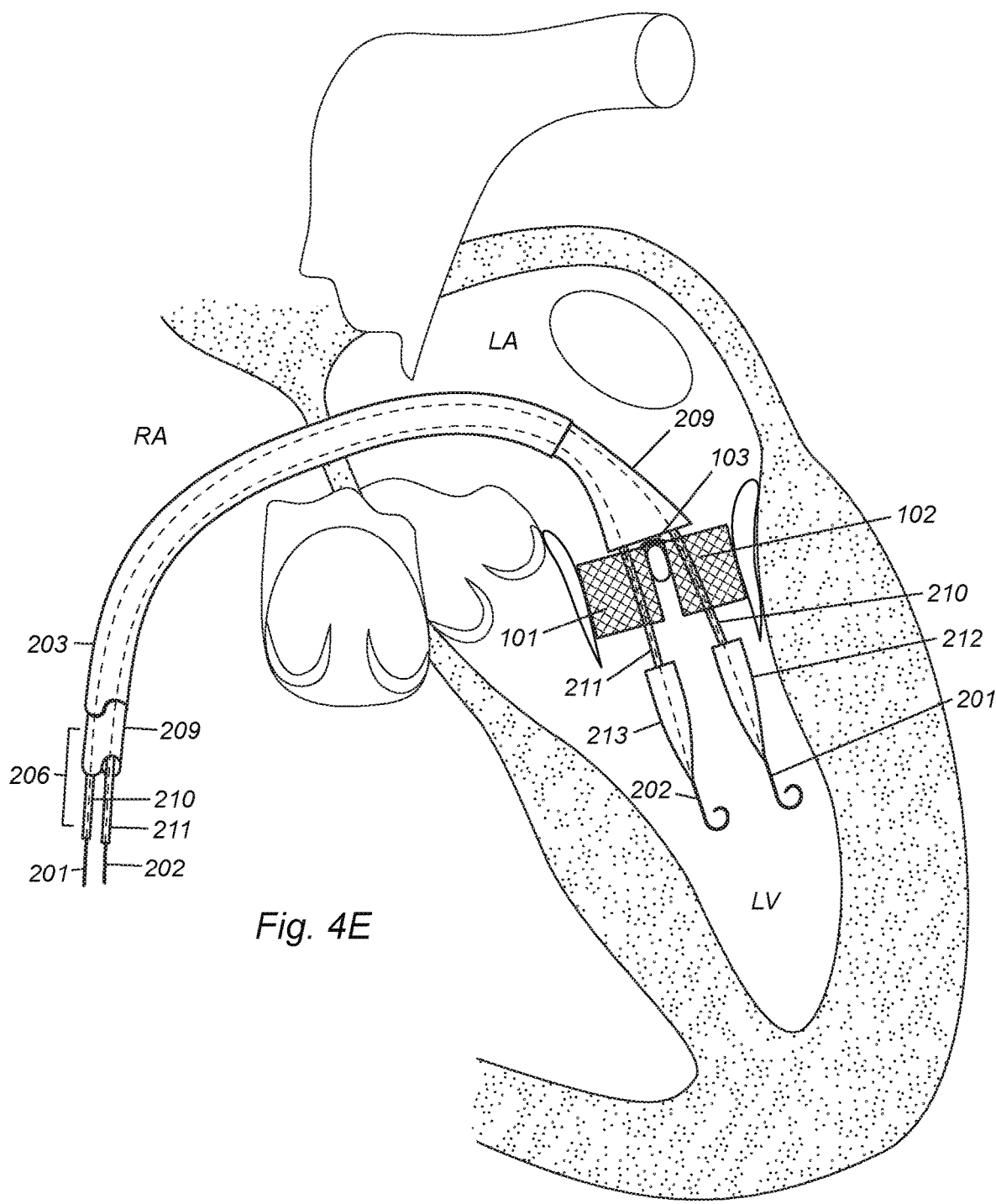

As shown in FIGS. 4C-D, a delivery catheter 206 (which may be 12-24 Fr) having an inverted Y-shaped enclosing sheath 207 at its distal end is inserted over the two guide wires (201 and 202) and into the sheath 203. In the delivery catheter 208, two catheters 210 and 211 are inserted into a cover 209 and over the two guide wires 201 and 202. The first and second replacement valves (101 and 102) of a DO-TMVR device may then be compressed and mounted near the distal ends of the two catheters 210 and 211. Then, distal to the two replacement valves 101 and 102, two enclosing caps 212 and 213 may be placed at the distal ends of the two catheters 210 and 211. In some embodiments, the two enclosing caps 212 and 213 enclose the two replacement valves 101 and 102 to keep them compressed. In this example, the two replacement valves may be connected via a connector 103 such as a hinge prior to delivery. The two replacement valves (101 and 102) are already connected via a connecting means 103 such as a hinge during the manufacturing process and are loaded onto the delivery catheter 208 as two connected valves. As illustrated in FIG. 4C, the delivery catheter 208 is guided to the double-orifice mitral valve so that a replacement valve (101 and 102) is placed in each orifice. In some embodiments, the two catheters 210 and 211 are advanced to expand the two replacement valves (101 and 102). As illustrated in FIG. 4E, after expansion of the replacement valves (101 and 102), a seal is formed between the two replacement valves (101 and 102) and the double-orifice mitral valve, and on the atrial side, the connector 103 such as a hinge is anchored over the connected middle of the anterior and posterior leaflets 106. The delivery catheter 204 is withdrawn via the sheath 203 out of the patient's body; the two guide wires (201 and 202) may be withdrawn via the sheath out of the patient's body; and the sheath 203 is withdrawn out of the patient's body. Additional standard steps that may be performed during the procedure include heparinization, and closure of the femoral vein either by manual compression, suture-mediated preclosure or surgical closure. The procedure may be performed by local anesthesia with conscious sedation or general anesthesia, in which case the patient is generally woken up immediately after the procedure. Heparinization may be reversed at the end of the procedure by administration of protamine. Heparin intolerant individuals may be anticoagulated during the procedure using direct thrombin inhibitors.

Example 5 Transapical Self-Expandable DO-TMVR

FIGS. 5A-E illustrate an example of transapical implantation of a DO-TMVR device. After induction of anesthesia, and sterile preparation, an apical incision may be performed by a standard procedure as described in Lichtenstein et al. Transapical transcatheter aortic valve implantation in humans: initial clinical experience. Circulation. 2006 Aug. 8; 114(6):591-6. Epub 2006 Jul. 31., which is incorporated by reference herein in its entirety.

In order to perform the procedure, the apex of the heart may be exposed for a surgical approach or punctured with a needle using a percutaneous approach. If a surgical approach is utilized, pledgeted sutures may be placed in a ring over the left ventricle (LV) apical surface. The percutaneous approach may be performed, for example, as described in in Dudiy et al. Percutaneous closure of left ventricular pseudoaneurysm, Circ Cardiovasc Interv. 2011 August; 4(4): 322-6. Epub 2011 Jul. 26, which is incorporated by reference herein in its entirety.

Figure 5A:
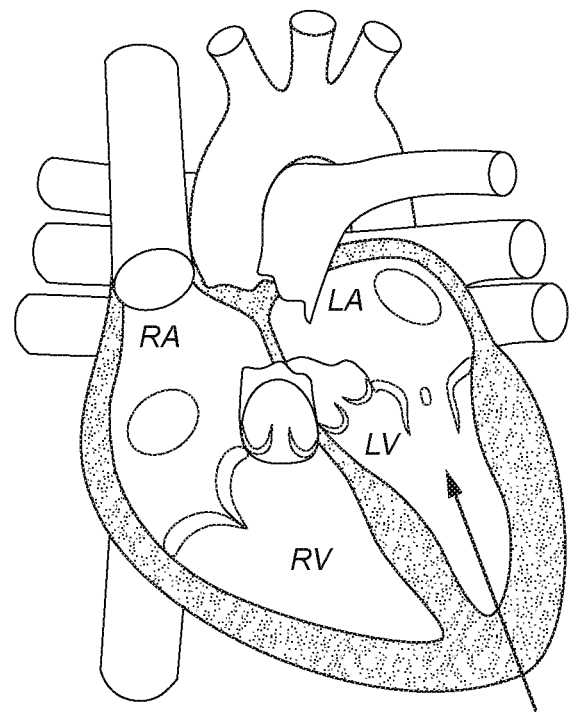
Figure 5B:
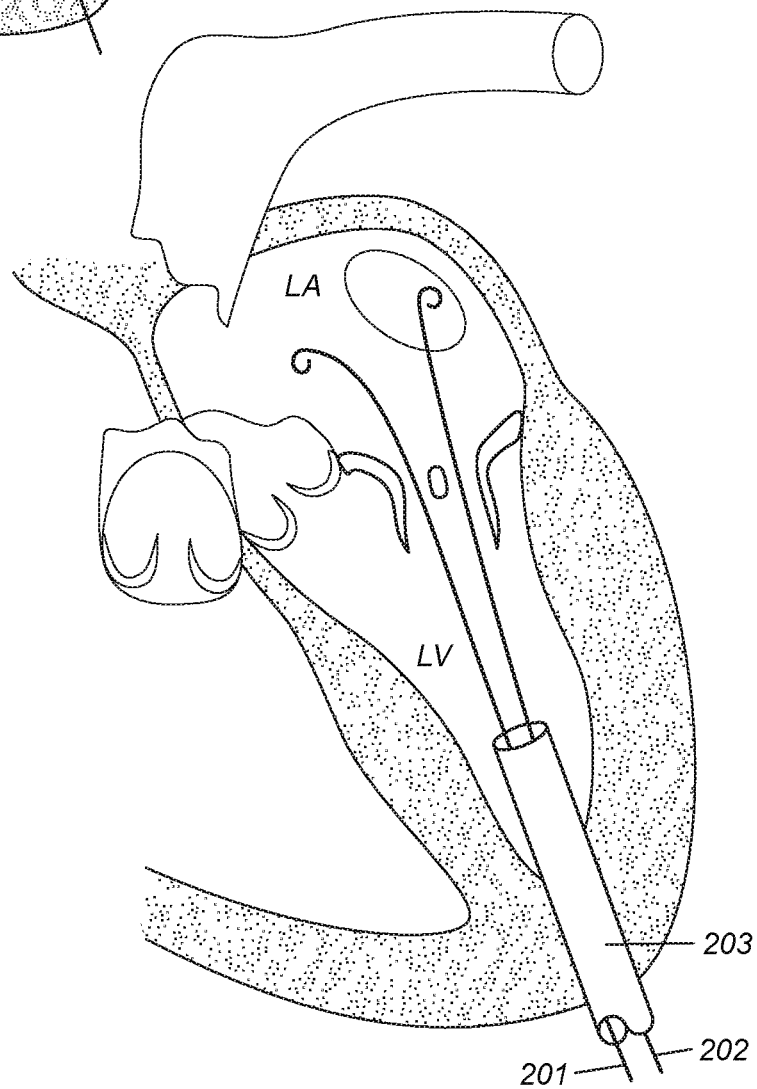

As illustrated in FIG. 5A, a needle of gauge 12-16 (shown as an arrow in FIG. 5A) may be utilized to puncture the LV apex. As illustrated in FIG. 5A, after puncture of the apex, a first guide wire 201 of caliber 0.014"-0.038" may be inserted through the needle, into LV, through one of the two orifices of the double-orifice mitral valve, and into LA. The needle may then be withdrawn. A sheath of size 4-7 Fr is inserted, and exchanged over a 0.035" or 0.038" wire to another sheath 203 of size 12-24 Fr, which is inserted over the guide wire into LV. As illustrated in FIG. 5B, a second guide wire 202 may be inserted into the sheath 203, into LV, through the other of the two orifices of the double-orifice mitral valve and into LA.

Figure 5E:
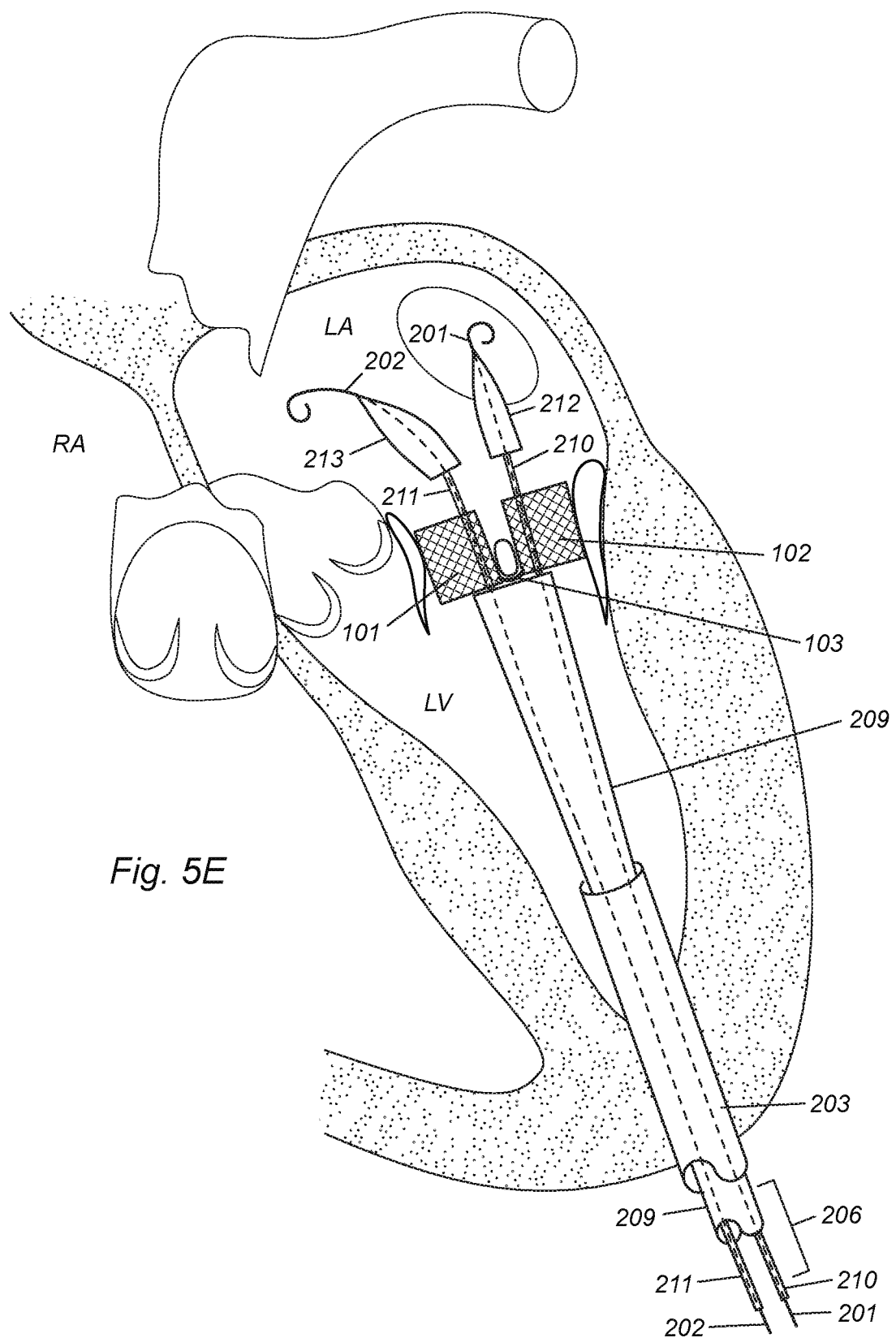
Figure 6A:
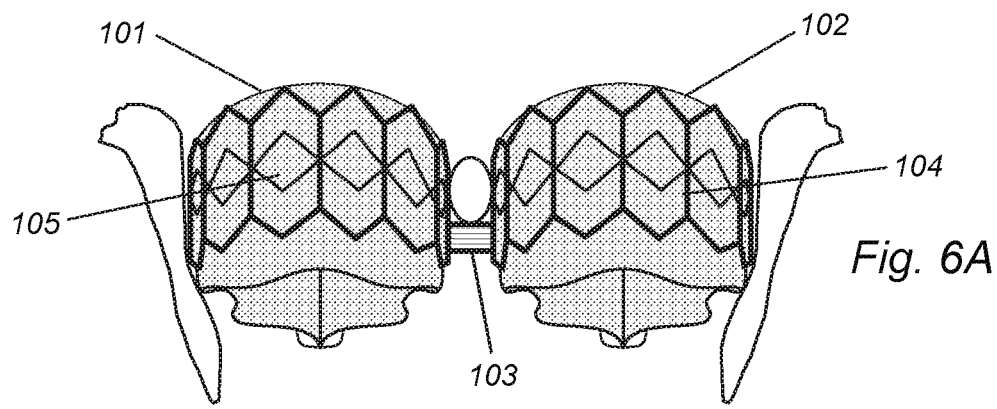
FIGS. 6A-D depict various perspective and cross sectional views of an embodiment of a DO-TMVR device comprising two balloon-expandable replacement valves.
Figure 6B:
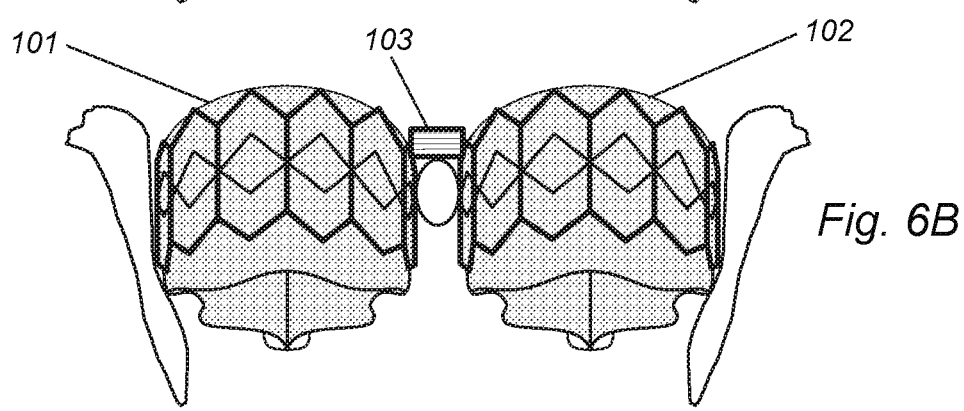
Figure 6C:
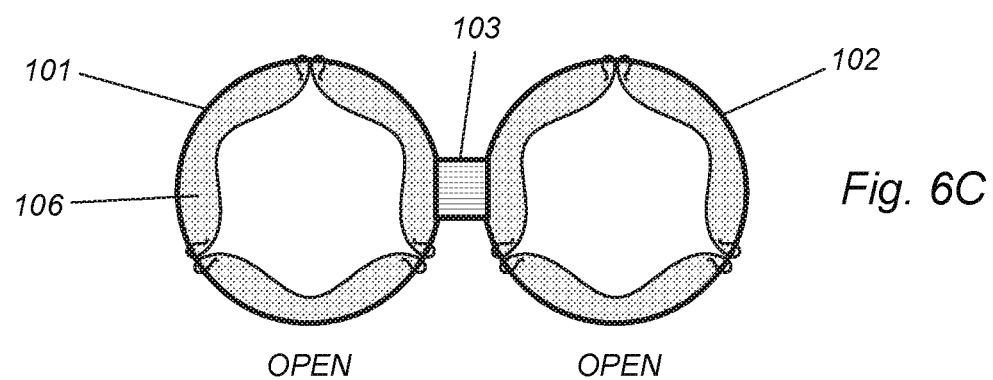
Figure 6D:
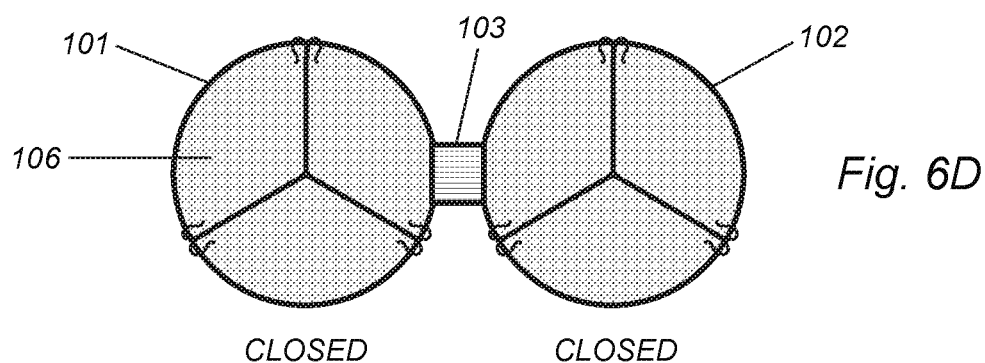
Figure 7A:
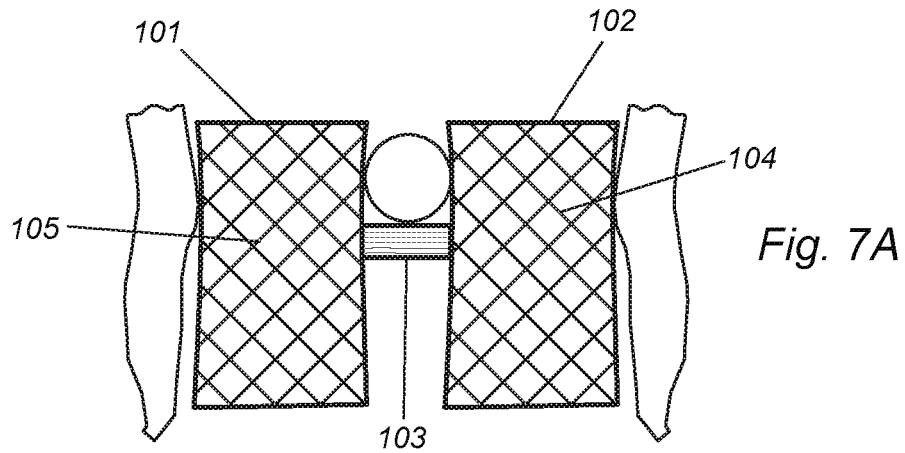
FIGS. 7A-D depict various perspective and cross sectional views of an embodiment of a DO-TMVR device comprising two self-expandable replacement valves.
Figure 7B:
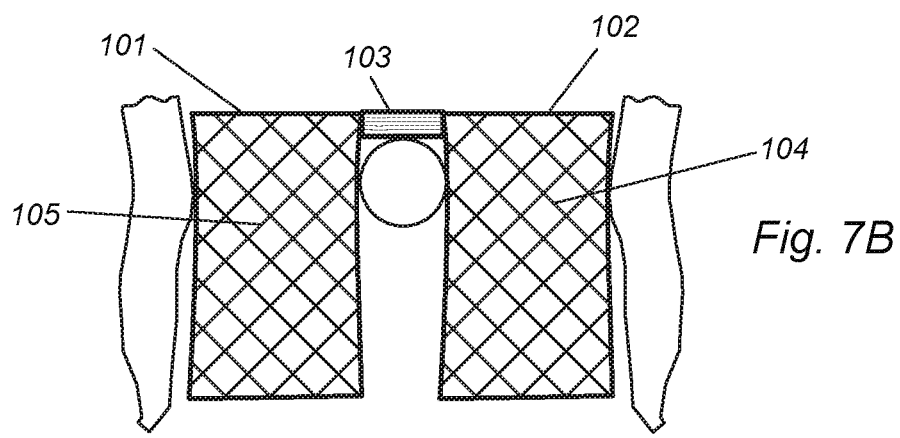
Figure 7C:
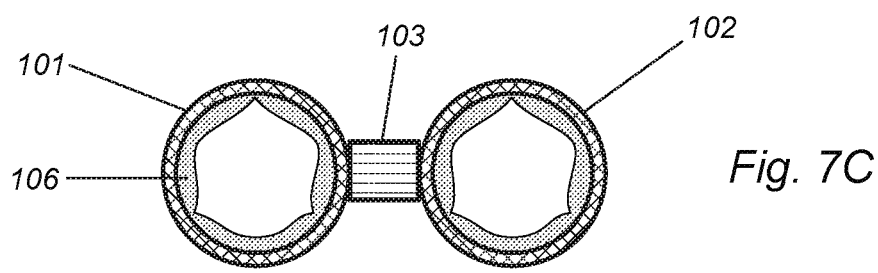
Figure 7D:
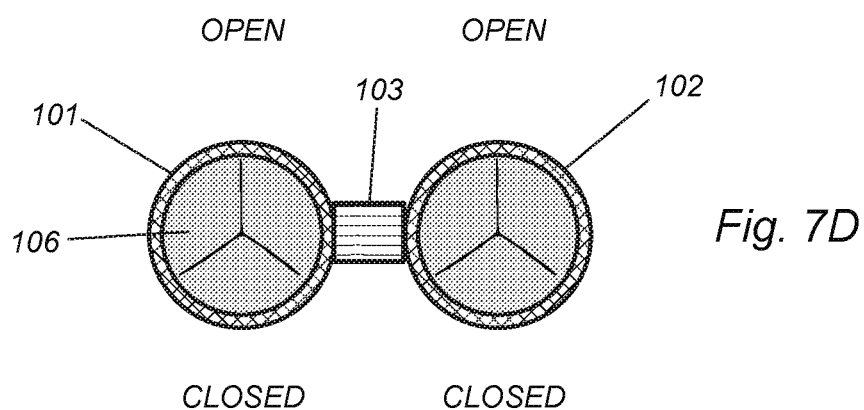
Figure 8A:
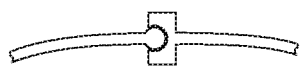
FIGS. 8A-C depict, in accordance with various embodiments, cross sectional views of three exemplar click-and-lock systems as non-limiting examples of a connectors for connecting the two replacement valves.
Figure 8B:
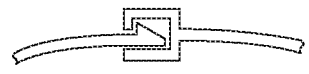
Figure 8C:
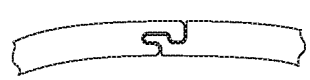

As shown in FIGS. 5C-D, a delivery catheter 206 (which may be 12-24 Fr) having an inverted Y-shaped enclosing sheath 207 at its distal end may be inserted over the two guide wires (201 and 202) and into the sheath (203). In the delivery catheter 204, two catheters 210 and 211 are inserted into a cover 209 and over the two guide wires 201 and 202. The first and second replacement valves (101 and 102) of DO-TMVR device are compressed and mounted near the distal ends of the two catheters 210 and 211. Further distal to the two replacement valves 101 and 102, two enclosing caps 212 and 213 are placed at the distal ends of the two catheters 210 and 211. The two enclosing caps 212 and 213 may enclose the two replacement valves 101 and 102 in order to keep them compressed. In this example, the two replacement valves 101 and 102 are connected via a connector 103 such as a hinge prior to delivery. The two replacement valves 101 and 102 are already connected via a connector 103 such as a hinge during the manufacturing process and are loaded onto the delivery catheter 204 as two connected valves 101 and 102. As illustrated FIG. 5C, the delivery catheter 204 is guided to the double-orifice mitral valve so that a replacement valve 101 and 102 is placed in each orifice. In some embodiments, the two catheters 210 and 211 are advanced to allow the two replacement valves 101 and 102 to expand. As illustrated in FIG. 5E, after of the expansion of the valves 101 and 102, a seal is formed between the two replacement valves 101 and 102 and the double-orifice mitral valve, and on the ventricular side, the connector 103 such as a hinge is anchored under the connected middle of the anterior and posterior leaflets. Then, the delivery catheter may be withdrawn via the sheath 203 out of the patient's body; the two guide wires 201 and 202 withdrawn via the sheath 203 out of the patient's body; and the sheath 203 is withdrawn out of the patient's body. Additionally, during the procedure, standard steps may be performed including heparinization and surgical closure of the apex, or by transcatheter approach with an Amplatzer or dedicated closure device. The procedure may be performed under general anesthesia. Heparinization may be reversed at the end of the procedure by administration of protamine. Heparin intolerant individuals may be anticoagulated during the procedure using direct thrombin inhibitors.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A device for transcatheter mitral valve replacement having a double orifice mitral valve in a subject who has undergone an edge-to-edge leaflet repair to bring leaflets of a native mitral valve together, thereby positioning a connected tissue of the leaflets at a middle portion of the connected leaflets, the device comprising:
   a first replacement heart valve having a first atrial side and a first ventricular side;
   a second replacement heart valve having a second atrial side and a second ventricular side; and
   a connector connecting the first and second replacement heart valves that are spaced,
   wherein the connector is configured to dissolve over time,
   wherein the connector is configured to use the connected tissue at the middle portion of the connected leaflets as an anchor,
   wherein each of the first and second replacement heart valves is substantially equivalent in size and sized to separately fit in one orifice of the double orifice mitral valve,
   wherein the connected first and second replacement heart valves are configured to fit together in the double orifice mitral valve created by the edge-to-edge leaflet repair, and
   wherein the device has a double orifice structure configured to anchor to the double orifice mitral valve created by the edge-to-edge leaflet repair such that the connector is anchored over or below the middle portion of the connected leaflets.

2. The device of claim 1, wherein the first and second replacement heart valves are connected on their atrial sides or ventricular sides with the connector comprising a hinge.

3. The device of claim 1, wherein the first and second replacement heart valves are configured to be unconnected and anchored separately to the tissue formed by each of two orifices of the double orifice mitral valve.

4. The device of claim 1, wherein the first and second replacement heart valves are connected halfway in between the ventricular and atrial sides or ⅓ of the way from the ventricular or atrial sides.

5. The device of claim 1, wherein the first replacement heart valve is a prosthetic valve or a bio-prosthetic valve and the second replacement heart valve is a prosthetic valve or a bio-prosthetic valve.

6. The device of claim 1, wherein the first replacement heart valve is self-expandable or balloon expandable and the second replacement heart valve is self-expandable or balloon expandable.

7. The device of claim 1, wherein the cross section of the first replacement valve is a circle or ellipse and the cross section of the second replacement valve is a circle or ellipse.

8. The device of claim 1, wherein each of the first and second replacement heart valves is cylindrical or the cross sections of the two replacement valves are two D-shapes with their straight sides opposing each other.

9. The device of claim 1, wherein each of the first and second replacement heart valves comprises stent frames made of iron, platinum, titanium, nickel, chromium, cobalt, magnesium, stainless steel, nitinol (nickel-titanium), nickel-chromium, cobalt-chromium, or platinum-iridium, or a combination thereof.

10. The device of claim 1, wherein the first replacement valve comprises one, two, three, or more leaflets and the second replacement valve comprises one, two, three, or more leaflets.

11. The device of claim 1, further comprising a delivery catheter.

12. The device of claim 11, wherein the delivery catheter has an inverted Y-shaped inflatable balloon or an inverted Y-shaped enclosing sheath at its distal end.

13. The device of claim 1, further comprising two guide wires, wherein a delivery catheter can be inserted over the two guide wires.

14. The device of claim 1, further comprising a sheath, wherein a delivery catheter can be inserted into the sheath.

15. The device of claim 1, wherein each of the first and second replacement heart valves is about 10 mm to 55 mm in height and about 10 mm to 55 mm in diameter.

16. The device of claim 1, wherein the first and second replacement heart valves are configurable to be connected prior to or after deployment of the device, and
   wherein a site and time of connecting the first and second replacement heart valves are based on access approach employed for device delivery, the access approach being transseptal or transapical delivery.

17. A device for transcatheter mitral valve replacement, the device comprising:
   a first replacement heart valve having a first atrial side and a first ventricular side; and
   a second replacement heart valve having a second atrial side and a second ventricular side, wherein each of the first and second replacement heart valves is about 10 mm to 55 mm in height and about 10 mm to 55 mm in diameter, wherein the first and second replacement heart valves are not directly connected to each other, wherein the first and second replacement heart valves are connected with a connector and configured to fit together in a double orifice mitral valve created by an edge-to-edge leaflet repair, wherein the connector, which is configured to use a connected tissue at a middle portion of connected leaflets of the mitral valve as an anchor, includes a U-shaped cross section conforming to the connected tissue to which the connector anchors, the connected tissue created at the middle portion by the edge-to-edge leaflet repair, and wherein the connector is configured to dissolve over time.

18. The device of claim 17, wherein each of the first and second replacement heart valves is substantially equivalent in size.

19. The device of claim 17, wherein the cross sections of the two replacement valves are two D-shapes with their straight sides opposing each other.

20. The device of claim 17, wherein the first and second replacement heart valves are connected halfway in between the ventricular and atrial sides or ⅓ of the way from the ventricular or atrial sides.

* * * * *